(12) United States Patent
Tremulis et al.

(10) Patent No.: US 8,556,963 B2
(45) Date of Patent: Oct. 15, 2013

(54) METHOD AND APPARATUS FOR TISSUE CONNECTION

(75) Inventors: William S. Tremulis, Redwood City, CA (US); Mahmood K. Razavi, Irvine, CA (US)

(73) Assignee: Mitral Interventions, Redwood City, CA (US)

( * ) Notice: Subject to any disclaimer, the term of this patent is extended or adjusted under 35 U.S.C. 154(b) by 953 days.

(21) Appl. No.: 12/503,173

(22) Filed: Jul. 15, 2009

(65) Prior Publication Data

US 2009/0276038 A1    Nov. 5, 2009

Related U.S. Application Data

(60) Continuation of application No. 12/348,663, filed on Jan. 5, 2009, which is a division of application No. 11/515,390, filed on Sep. 1, 2006, now Pat. No. 7,618,449, which is a continuation of application No. 10/461,861, filed on Jun. 12, 2003, now Pat. No. 7,101,395, which is a continuation-in-part of application No. 10/232,753, filed on Aug. 30, 2002, now Pat. No. 7,125,421.

(60) Provisional application No. 60/388,250, filed on Jun. 12, 2002.

(51) Int. Cl.
*A61F 2/24* (2006.01)

(52) U.S. Cl.
USPC ............................ 623/2.11; 606/232; 606/151

(58) Field of Classification Search
USPC ......... 606/213, 228–232, 139, 144–148, 151, 606/153, 158, 219, 222–224; 623/23.72; 128/898

See application file for complete search history.

(56) References Cited

U.S. PATENT DOCUMENTS

| 4,042,979 | A |   | 8/1977  | Angell |
|-----------|---|---|---------|--------|
| 4,743,253 | A |   | 5/1988  | Magladry |
| 4,917,698 | A |   | 4/1990  | Carpentier et al. |
| 5,067,957 | A |   | 11/1991 | Jervis |
| 5,123,914 | A | * | 6/1992  | Cope ............................. 606/232 |
| 5,258,000 | A | * | 11/1993 | Gianturco ..................... 606/151 |
| 5,261,914 | A | * | 11/1993 | Warren ......................... 606/323 |
| 5,356,424 | A | * | 10/1994 | Buzerak et al. ............... 606/223 |
| 5,441,517 | A |   | 8/1995  | Kensey et al. |
| 5,476,500 | A |   | 12/1995 | Fain et al. |
| 5,477,864 | A |   | 12/1995 | Davidson |
| 5,486,183 | A |   | 1/1996  | Middleman et al. |
| 5,562,685 | A | * | 10/1996 | Mollenauer et al. .......... 606/144 |
| 5,582,616 | A | * | 12/1996 | Bolduc et al. ................. 606/143 |

(Continued)

FOREIGN PATENT DOCUMENTS

| EP | 0 257 874 | 2/1988 |
| EP | 0 595 791 | 5/1994 |

(Continued)

*Primary Examiner* — Corrine M McDermott
*Assistant Examiner* — Mark Mashack
(74) *Attorney, Agent, or Firm* — Goodwin Procter LLP

(57) ABSTRACT

A tissue connecting device is provided. The device comprise an elongate delivery device having a lumen, a proximal end, and a distal end. The distal end is configured to engage tissue and advance the device into tissue. At least one anchor deliverable through a lumen of the elongate delivery device. The distal end of the device may be designed to engage tissue upon rotation of the device about its longitudinal axis.

18 Claims, 30 Drawing Sheets

(56) References Cited

U.S. PATENT DOCUMENTS

| | | | |
|---|---|---|---|
| 5,584,879 A | 12/1996 | Reimold et al. | |
| 5,626,611 A * | 5/1997 | Liu et al. | 606/230 |
| 5,693,092 A | 12/1997 | Silvestrini et al. | |
| 5,709,692 A * | 1/1998 | Mollenauer et al. | 606/141 |
| 5,716,397 A | 2/1998 | Myers | |
| 5,810,851 A * | 9/1998 | Yoon | 606/148 |
| 5,820,631 A * | 10/1998 | Nobles | 606/213 |
| 5,824,008 A * | 10/1998 | Bolduc et al. | 606/143 |
| 5,846,261 A | 12/1998 | Kotula et al. | |
| 5,871,501 A | 2/1999 | Leschinksy et al. | |
| 5,876,373 A | 3/1999 | Giba et al. | |
| 5,972,001 A * | 10/1999 | Yoon | 606/139 |
| 6,036,701 A * | 3/2000 | Rosenman | 606/151 |
| 6,080,182 A | 6/2000 | Shaw et al. | 606/213 |
| 6,123,084 A | 9/2000 | Jandak et al. | |
| 6,165,183 A | 12/2000 | Kuehn et al. | |
| 6,183,512 B1 | 2/2001 | Howanec, Jr. et al. | |
| 6,290,674 B1 | 9/2001 | Roue et al. | |
| 6,312,447 B1 | 11/2001 | Grimes | |
| 6,328,727 B1 | 12/2001 | Frazier et al. | |
| 6,402,736 B1 | 6/2002 | Brown et al. | |
| 6,402,781 B1 | 6/2002 | Langberg et al. | |
| 6,416,548 B2 | 7/2002 | Chinn et al. | |
| 6,419,696 B1 | 7/2002 | Ortiz et al. | |
| 6,451,024 B1 * | 9/2002 | Thompson et al. | 606/104 |
| 6,506,190 B1 * | 1/2003 | Walshe | 606/139 |
| 6,547,787 B1 | 4/2003 | Altman et al. | |
| 6,595,911 B2 | 7/2003 | LoVulo | |
| 6,602,288 B1 | 8/2003 | Cosgrove et al. | |
| 6,651,672 B2 | 11/2003 | Roth | |
| 6,656,178 B1 | 12/2003 | Veldhuizen et al. | |
| 6,663,633 B1 * | 12/2003 | Pierson, III | 606/148 |
| 6,723,107 B1 * | 4/2004 | Skiba et al. | 606/144 |
| 7,044,967 B1 | 5/2006 | Solem et al. | |
| 7,087,064 B1 * | 8/2006 | Hyde | 606/142 |
| 7,445,634 B2 * | 11/2008 | Trieu | 623/17.11 |
| 7,536,228 B2 | 5/2009 | Shaolian et al. | |
| 7,611,521 B2 * | 11/2009 | Lubbers et al. | 606/104 |
| 7,632,308 B2 | 12/2009 | Loulmet | |
| 2002/0077631 A1 * | 6/2002 | Lubbers et al. | 606/72 |
| 2002/0151961 A1 | 10/2002 | Lashinski et al. | |
| 2002/0173841 A1 | 11/2002 | Ortiz et al. | |
| 2003/0220685 A1 * | 11/2003 | Hlavka et al. | 623/2.11 |
| 2004/0039392 A1 * | 2/2004 | Trieu | 606/86 |
| 2004/0049211 A1 | 3/2004 | Tremulis | |
| 2004/0088047 A1 | 5/2004 | Spence et al. | |
| 2004/0098047 A1 | 5/2004 | Frazier et al. | |
| 2004/0127982 A1 | 7/2004 | Machold et al. | |
| 2006/0142787 A1 | 6/2006 | Weller et al. | |
| 2007/0080188 A1 * | 4/2007 | Spence et al. | 227/175.1 |

FOREIGN PATENT DOCUMENTS

| | | |
|---|---|---|
| EP | 0958795 | 11/1999 |
| EP | 1 088 529 | 4/2001 |
| FR | 2 799 364 | 10/1999 |
| WO | WO 91/07928 | 6/1991 |
| WO | WO 97/03625 | 2/1997 |
| WO | WO 97/10757 | 3/1997 |
| WO | WO 97/27898 | 8/1997 |
| WO | WO 00/60995 | 10/2000 |
| WO | WO 01/21247 | 3/2001 |
| WO | WO 01/72239 | 10/2001 |
| WO | WO 02/03892 | 1/2002 |
| WO | WO 02/28321 | 4/2002 |
| WO | WO02/058599 * | 8/2002 |

* cited by examiner

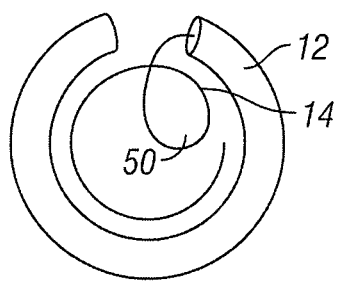
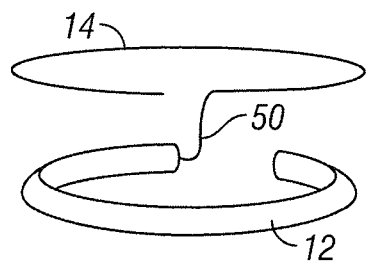
FIG. 8A  FIG. 8B
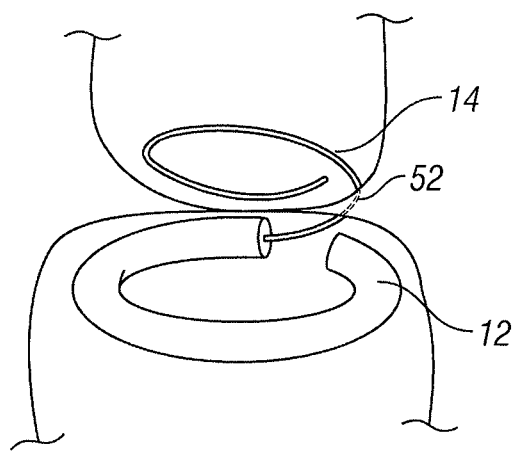
FIG. 9
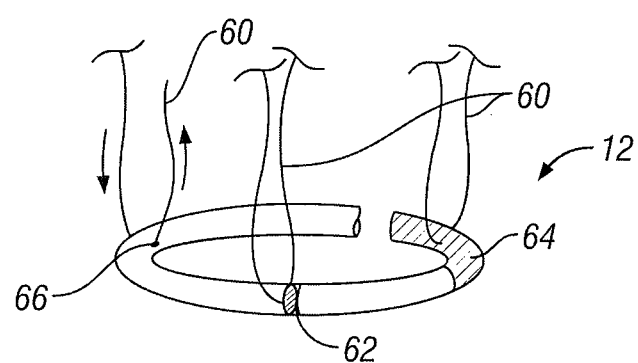
FIG. 10A

Spherical Bulbs    Hockey Stick Feet    Zig-Zag Feet

METHOD AND APPARATUS FOR TISSUE CONNECTION

CROSS-REFERENCE TO RELATED APPLICATIONS

The present application is a continuation of U.S. Ser. No. 12/348,663 filed Jan. 15, 2009, which is a divisional of U.S. Ser. No. 11/515,390 filed Sep. 1, 2006 (U.S. Pat. No. 7,618,449), which is a continuation of U.S. Ser. No. 10/461,861 filed Jun. 12, 2003 (U.S. Pat. No. 7,101,395), which is a continuation in part of U.S. Ser. No. 10/232,753 filed Aug. 30, 2002 (U.S. Pat. No. 7,125,421), which claims the benefit of U.S. Ser. No. 60/388,250 filed Jun. 12, 2002, all of which applications are fully incorporated herein by reference.

BACKGROUND OF THE INVENTION

1. Field of the Invention

This invention relates generally to medical devices, and their methods of use, and more particularly to devices, and methods of use, utilized for the repair and reconnection of various tissues of the body. The present invention may be useful in a variety of applications including but not limited to minimally invasive devices and methods for repair or reshaping of improperly functioning heart valves or heart tissue.

2. Description of Related Art

Bringing together tissues in closer proximity to one another is a typical means for closing wounds such as catheter puncture sites during percutaneous procedures (angioplasty, stenting, endograft procedures and the like), as well as in stomach stapling for the morbidly obese, gastrostomy placement, etc. Although these procedures all may benefit from the inventions described herein, one particularly useful and immediate benefit for these devices, methods and systems is in the bringing together, or coaptation, of heart valve leaflets so that they close properly against the relatively high pressures during the contraction of the heart muscle so as to improve the pumping efficiency of the heart muscle. Furthermore, the present invention additionally provides new and novel devices, methods and systems for the percutaneous endovascular repair of the valves of the heart and for their modification and subsequent improvement in cardiac valve function.

Mitral valve regurgitation is a condition in which the leaflets of the heart valve do not properly close during contraction (systole) of the heart. This permits blood to flow in a retrograde fashion from the ventricle of the heart back into the atrium of the heart. The pumping efficiency of the heart is compromised and the result, if left unchecked, can be progressive heart failure resulting in extreme fatigue or worse and the inability of the patient to lead a normal life.

Although there are numerous reasons for damage to the valves of the heart, the typical treatment is often surgery. During surgical repair of the valves, the chest is usually opened, at least in part, to allow enough room for the surgeon to perform a repair or replacement of the damaged valve. This usually requires that the patient be placed on a bypass machine to pump the blood while the surgeon operates on the stopped heart muscle. For obvious reasons, this can be very traumatic on the patient and recovery may take many months. Additionally, surgery may not be an option for some patients due to limited possibility for recovery, concurrent disease, or age.

For these reasons, it would be desirable to provide an alternative to open heart surgery to modify, repair or replace a damaged heart valve without requiring the patient's chest to be opened and/or the patient placed on bypass during the procedure.

SUMMARY OF THE INVENTION

The present invention provides new and novel devices, methods and systems for the repair of the valves and for their modification and subsequent improvement in valve function. More specifically, in some embodiments, the present invention achieves these repairs using percutaneous endovascular techniques that minimize trauma to the patient and provide reduced recovery time and recovery cost.

In one aspect of the present invention, a tissue connecting device is provided. The device comprise an elongate delivery device having a lumen, a proximal end, and a distal end. The distal end is configured to engage tissue and advance said device into tissue. At least one anchor deliverable through a lumen of the elongate delivery device. The distal end of the device may be designed to engage tissue upon rotation of the device about its longitudinal axis.

In a still further aspect of the present invention, a kit is provided for delivering a tissue connection device to a valve having an annulus and a plurality of leaflets. The kit may include an elongate member having a first substantially linear configuration when engaged with an elongate delivery device and a second substantially circular configuration defining a first support ring and a second support ring when the member disengages from the delivery device. The kit may further include instructions for use describing a method for connecting the elongate member to the valve and a package for holding the elongate member and the instructions for use.

A further understanding of the nature and advantages of the invention will become apparent by reference to the remaining portions of the specification and drawings.

BRIEF DESCRIPTION OF THE FIGURES

FIGS. 8A and 8B are top and side views of another annular support device.

FIG. 9 shows the device of FIG. 1 penetrating tissue.

FIGS. 10A-10C show the use of sutures on annular support rings in accordance to the present invention.

DESCRIPTION OF THE SPECIFIC EMBODIMENTS

Figure 1:
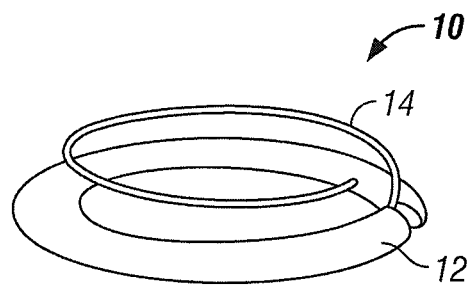
FIG. 1 is perspective view of an annular support device.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

The present invention provides new and novel devices, methods and systems for the repair of a valve and for their modification and subsequent improvement in valve function. More specifically, in some embodiments, the present invention achieves these repairs using percutaneous endovascular techniques that minimize trauma to the patient and provide reduced recovery time and cost. One particularly useful and immediate benefit for these devices, methods and systems is in the bringing together, or coaptation, of heart valve leaflets so that they close properly against the relatively high pressures during the contraction of the heart muscle so as to improve the pumping efficiency of the heart muscle.

In the various embodiments, the devices, methods and systems of the present invention provide connection and/or reconnection of body tissues, whether disconnected by trauma, surgery, disease, normal anatomy, or other means, although the devices described herein may, in fact, be used during open-heart surgery or minimally invasive heart surgery. By way of illustration, and without limitation, the devices, methods and systems are useful for the repair of the atrioventricular valves of the heart, particularly the mitral valve. In one embodiment, it may be desirable to perform the repair endovascularly, advancing the devices and systems through the major blood vessels leading to and exiting from the heart, and using these conduits as natural pathways for the devices to access the valves of the heart. Although the repair of the mitral valve will be discussed in detail, it can be appreciated that the devices, methods and systems described herein can easily be adapted to repair, connect, or bring other various body tissues into closer proximity to one another. At least some of these objectives will be met by the novel inventions, devices, methods and systems described hereinbelow. Those skilled in the art will immediately recognize that various combinations, modifications, and equivalents of the inventions described herein can be used without departing from the scope of these inventions.

Referring now to FIG. 1, in one embodiment of the present invention, a tissue connection device 10 suitable for minimally invasive delivery comprises a first support ring or annular support ring 12 and a second support ring or attached clamp 14 that secures the ring 12 to the opposite sides of the valve tissue. The first support ring 12 provides support for the annular ring of tissue surrounding the heart valve or other target site so that proper coaptation may occur with the valve leaflets (see FIG. 5). As seen in the embodiment of FIG. 1, the first support ring 12 may be substantially in a first plane while the second support ring 14 may be substantially in a second plane roughly parallel to the first plane.

Figure 2:
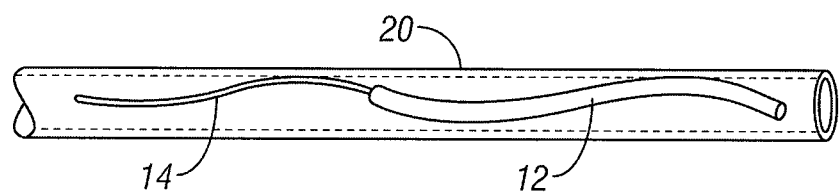
FIGS. 2-5 illustrate the delivery of the device of FIG. 1 to a treatment site.

Referring now to FIG. 2, delivery of the device 10 may be accomplished by straightening the first support ring 12 and second support ring or clamp 14 and inserting device 10 through an elongate delivery device 20 such as, but not limited to, a guide catheter that may be used to access the chambers of the heart. As seen in FIG. 2, the device 10 is an elongate member that assumes a substantially linear configuration when placed inside an appropriately sized guide catheter. In one embodiment, the guide catheter may be sized between about 3 and 15 French (1 mm to 5 mm diameter). When the device 10 is removed from the delivery device 20, the tissue connection device 10 may assume a coiled configuration as shown in FIG. 1.

Figure 3:
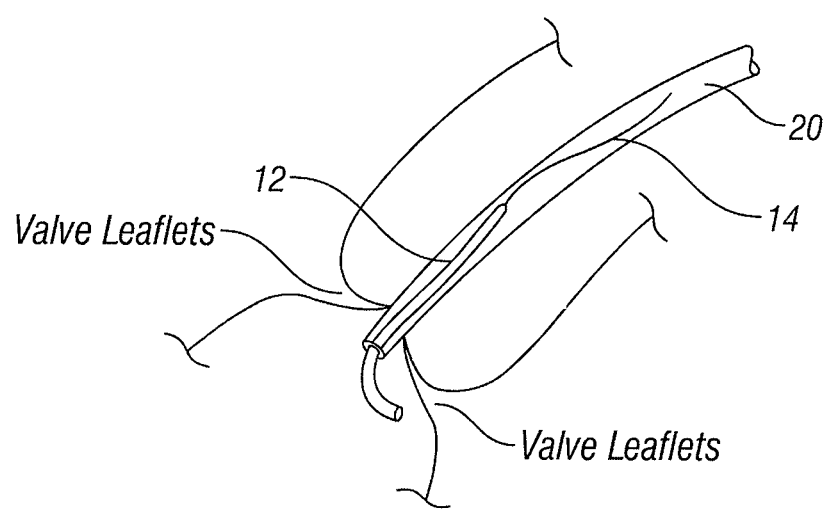

Referring now to FIG. 3, the delivery device 20 such as a guide catheter may be inserted at a location remote from the heart such as the femoral artery, brachial artery, inferior vena cava, jugular vein, etc. In this example, delivery device 20 is then advanced through the vessel to the heart and across the target valve. As the device 10 in a straightened ring or linear configuration is advanced out the distal end of the catheter, the device 10 begins to regain its preformed coil or circular shape.

Figure 4:
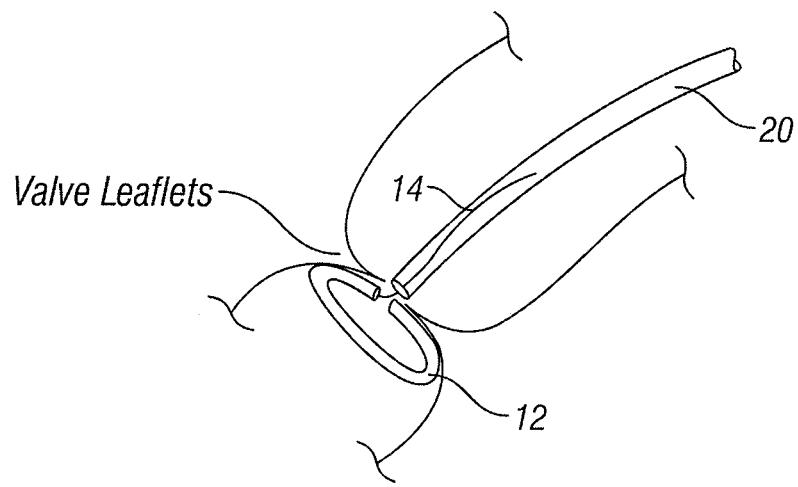

Referring now to FIG. 4, following deployment of the first support ring 12, the delivery device 20 is pulled back to the proximal side of the valve where the clamp portion or second support ring 14 of the device 10 is deployed.

Figure 5:
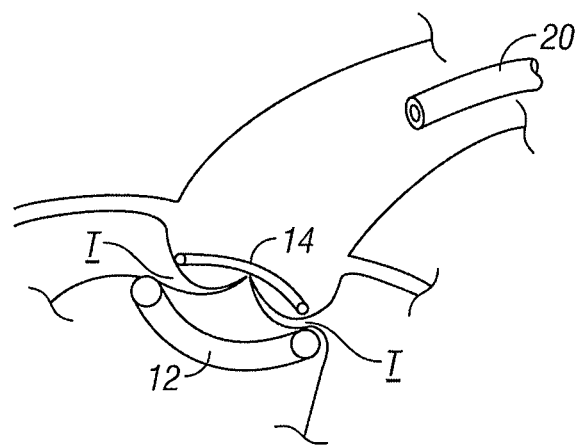

As seen in FIG. 5, the tissue connection device 10 when deployed in the heart valve captures a tissue T between the first support ring 12 and the second support ring 14. The clamping action of device 10 reduces the dilation of the valve formed by tissue T, thus urging the leaflets closer to the center of the valve. It should be understood that, in some embodiments, configuration may be reversed where the second support ring 14 is on the bottom of the valve and the first support ring 12 is located on top. Furthermore, as seen in FIGS. 1-5, the first support ring 12 may be thicker or have a greater radial thickness than the radial thickness of the second support ring 14. The greater radial thickness may provide improved support or capture to tissue engaged between the rings. Additionally, the second support ring 14 having a smaller radial thickness may be more easily situated on sides of the valve with chordae or other materials that may interfere with proper device seating. Still further, as discussed for FIGS. 7A and 7B, the varying thicknesses may also provide a desired reshaping of tissue captured between the rings 12 and 14 to reduce dilation of the valve tissue.

Figure 6:
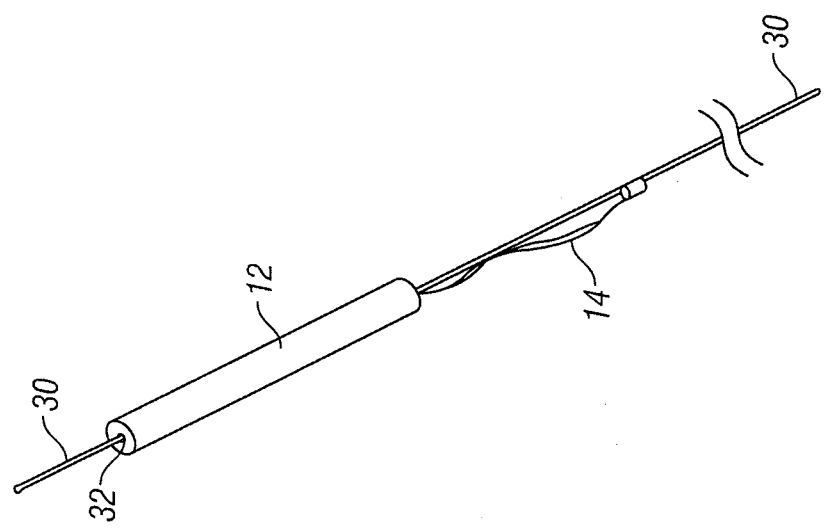
FIG. 6 shows another embodiment of present invention for use with a straightening mandrel.

Referring now to FIG. 6, in another embodiment of the present invention, the device 10 may be configured for use with a straightening mandrel 30 that is used as a delivery device 20 to deploy the device 10 to the target site. As seen in FIG. 6, the straightening mandrel 30 may pass through a lumen 32 in the first support ring 12 and a guide loop on the second support ring 14. Thus in this embodiment, the tissue connection device is constrained through internal straightening parts instead of externally constraining parts when a guide catheter is used. The device 10 is loaded onto a straightening mandrel 30 or guide wire for delivery and upon removal of the mandrel or guide wire, the annuloplasty ring and/or clamp reverts back to its pre-determined remembered shape, typically in its valve supportive configuration. The hollow device 10 and its removable straightening guide wire/mandrel are also adaptable for use with each of the other designs described within this specification, and is not limited to just the annuloplasty ring and clamp configurations.

Figure 7A:
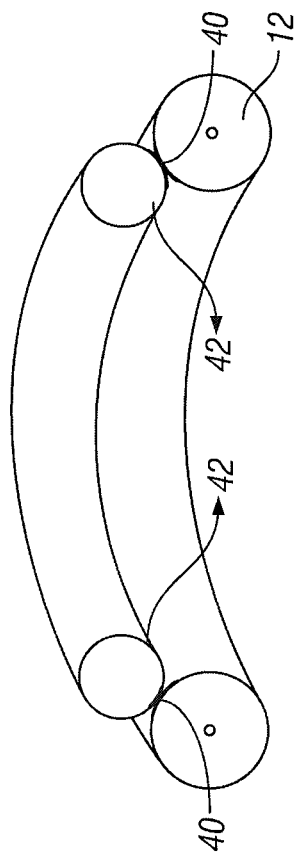
FIGS. 7A and 7B show cross-sectional views of interaction between two support rings to engage tissue therebetween.
Figure 7B:
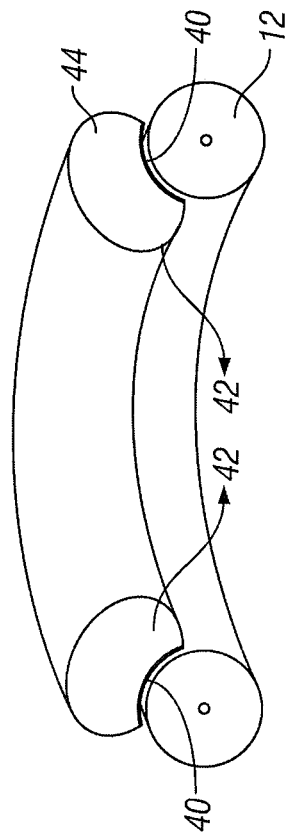

Referring now to FIGS. 7A and 7B, another embodiment of the present invention will now be described. For ease of illustration, the rings are shown to be touching. It should be understood that tissue may be engaged between the rings and captured therebetween. In the embodiment of FIG. 7A, the first support ring 12 has a larger circumference than the second support ring 14. The ring 14 engages an inner circumferential surface 40 of the first support ring 12. This provides a radially inward force as indicated by arrows 42 on an tissue captured between the rings. The outer ring, in this case first support ring 12, may engage the tissue first and then the second ring 14 will engage the tissue and pull it inward. For heart valve reshaping, this will bring the valve leaflets closer to the center and reduce dilation of the valve to minimize leakage and regurgitation.

FIG. 7B shows another embodiment where the ring 44 has substantially the same diameter or circumference as the first support ring 12. The ring 44, however, has a cross-sectional geometry wherein the ring 44 only engages the inner circumferential surface 40 of the first support ring 12. Again, the rings will draw tissue radially inward as indicated by arrows 42.

Referring now to FIGS. 8A and 8B, the connection between the support ring 12 and the clamping ring 14 may have variations depending on the valve anatomy, location, and disease condition. For instance in one embodiment, it may be desired to have the connection between the two structures in the center of the valve such that there is no interference with the movement of the valve leaflets (FIGS. 8A and 8B). A portion 50 of the tissue connection device will be configured to extend through the center of the valves.

Referring now to FIG. 9, an alternative embodiment of the present invention has a portion 52 of the elongate member that transverses through the leaflet tissue towards its most outer edge where there would be little or no interference with the valve leaflet. Additionally, this position for the connection would allow the entire device to remain out of the flow of blood through the valve opening. This would have the advantage of no disruption of blood flow through the valve and minimizes bloodstream turbulence and the potential formation and/or dislocation of blood clots around the device.

Figure 10B:
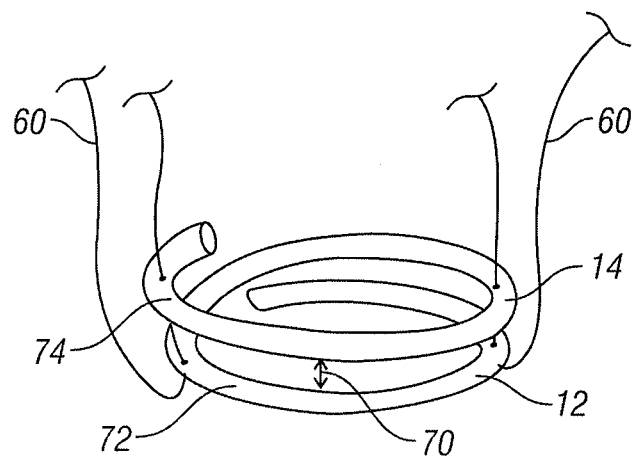
Figure 10C:
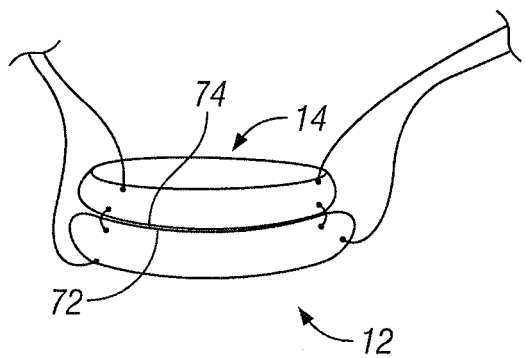

Referring now to FIGS. 10A through 10C, to aid in the proper seating or apposition of the valve annular support structure against the valve tissue, detachable threads or sutures may be attached at various points around the device. As seen in FIG. 10A following deployment of the distal structure, whether first support ring 12 or second support 14, the threads or sutures 60 may be pulled proximally towards the guide catheter, thereby properly seating the structure to the underside of the valve. At least one thread or suture 60 would aid in proper seating, preferably three, so that the orientation of the structure could be adjusted against the valve. The location of each thread or suture 60 on the structure may be identified with unique radiopaque markers 62 to help in the choice of which part of the structure and which corresponding thread needs additional tension for optimum valve support. After positioning the device 10 but before permanent deployment, the improvement in valve function may be assessed. Valve function may be assessed by any suitable means such as angiography, magnetic resonance imaging, ultrasound imaging, trans-esophageal echocardiography and the like. Following verification of improved valve function, one end of the releasable thread could be pulled, removing the thread from its connection to the valve support structure. (See FIG. 37 for removal of thread.)

Materials used in the construction of the annular support ring 12 or the second support ring/clamping device 14 include, but are not limited to, Nitinol, superelastic metallic alloys and plastics, PTFE, silicone, stainless steel, ceramics and/or other suitable materials or combinations thereof. Additionally, shape-memory alloys and plastics may be used for the support structure and/or the clamping structure in order for the device to be delivered in a straightened condition and, when heated to a temperature above its transition temperature, the valve support structure and/or the clamping structure assume their predetermined geometries. In one embodiment, the temperature of the body would be sufficient to transform the shape of the shape-memory material into its ring and clamp configuration. In another embodiment, energy is applied to the device using electrical, radio frequency, microwave, heated solutions passed through the guide catheter, or other suitable energy source to transform the shape-memory material to its remembered clamping and support shape. Still further, the exterior surface of the first support ring 12 or second support ring 14 may be conditioned to accept penetration or engagement with a needle carrying a suture. As seen in FIG. 10A, the surface may have a mesh or other covering 64 to facilitate coupling with sutures 60. The mesh may be made of a variety of materials such as Dacron® or other suitable material. For ease of illustration, only a portion of the ring 12 is shown to be covered with mesh, though it should be understood that the entire ring may be covered with mesh. Other methods may also be used to facilitate such eyelets, apertures 66, anchoring locations, or connection devices on the ring 12. The ring 12 may also be made entirely of a penetrable material so that sutures may be easily placed in the device. The ring material may also be made porous in order to promote endothelialization of the ring around the valve. A more secure device may aid in the support the implantable ring provides to the valve tissues. Suitable materials for the ring include Nitinol, ceramics, and plastic polymers. Additionally the materials used may elude drugs that may assist in the promotion of endothelialization. Alternatively, the ring may be surrounded by materials such as polyester that promotes tissue ingrowth and endothelialization of the device.

Referring now to FIG. 10B, in another embodiment of the device 10, sutures 60 may be secured to both the first support ring 12 and the second support ring 14 such that, when in its desired position, the sutures apply additional force to the rings 12 and 14 in order to increase the clamping force between the two structures and provide additional support to the valve's annular ring. When delivered, the first support ring 12 and second support ring 14 are spaced apart by a distance 70, wherein a first ring tissue engaging surface 72 is separated from a second ring tissue engaging surface 74.

To secure the clamp section 14 and the support section 12 together, a knot and/or a clamp (or alternate securing means) for each suture 60 is advanced from outside the body, through a guide catheter, and to the device using any one of several knot-tying techniques and/or tools commonly used in vessel closure devices. Additionally, a portion of the suture material 60 may be elastic in order to provide a constant force to the support structure so that during the normal contractions of the heart, the device 10 is allowed limited movement relative to the valve. As seen in FIG. 10C, the device 10 when sutured together may engage tissue captured between surfaces 72 and 74 to reform the valve tissue as desired.

Figure 11:
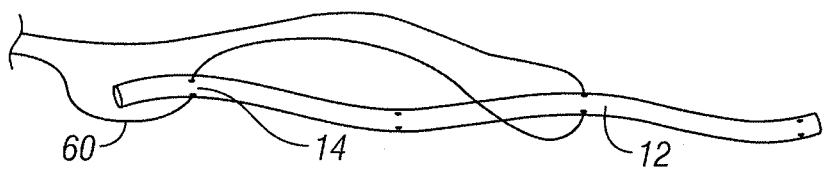
FIG. 11 shows the attachment of sutures to a support ring in a linear configuration.

Referring now to FIG. 11, the device 10 as delivered through a guide catheter 20 with sutures attached, would look similar to the referenced illustration. Each of the pre-threaded sutures 60 attached to the ring structure 12 line up with the corresponding points on the clamp 14 that are located immediately adjacent to the ring attachment points when in its delivered configuration. This facilitates placement and clamping of the device 10.

Figure 12:
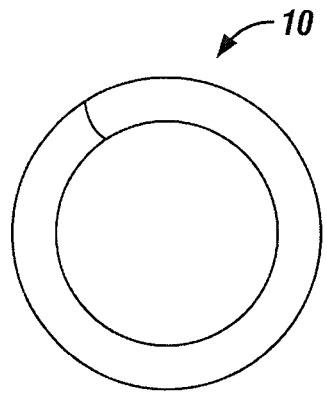
FIGS. 12-13B show various geometries of the support ring.
Figure 13A:
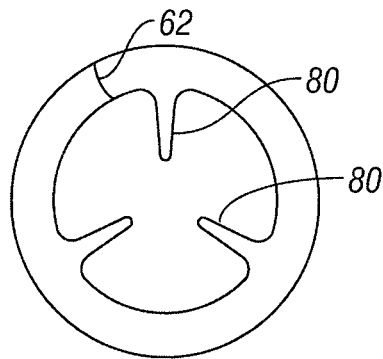
Figure 13B:
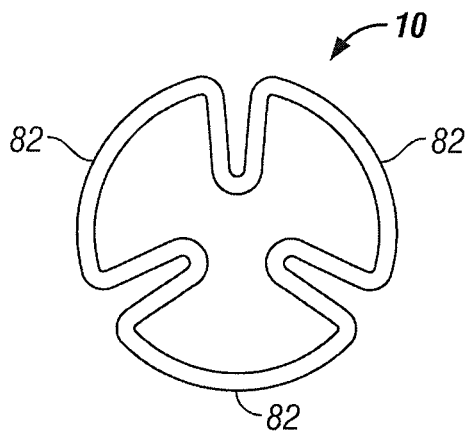

Referring now to FIG. 12, the standard ring-shaped coil device 10 described is only one configuration that may be delivered in a straight configuration and provide support for the valve or target tissue when delivered to its destination. Other shapes may provide additional support for one or more leaflets of the valve or may provide additional support to a damaged portion of the heart valve annulus. For example in FIG. 13A, inner extensions 80 on the ring may provide a backboard for the leaflets preventing prolapse of the valve leaflet during systole of the heart. In another embodiment as seen in FIG. 13B, the ring 12 may be shaped more like a bi-lobed leaf for the mitral valve, or a shamrock or cloverleaf configuration 82 for the three-leaflet tricuspid valve of the heart. The additional inner structure(s) of the cloverleaf configuration 82 provides the valve leaflet with an area that it cannot physically go beyond, ensuring proper coaptation of it and its counterpart leaflet against its corresponding stop on the opposite side of the valve.

Figure 14A:
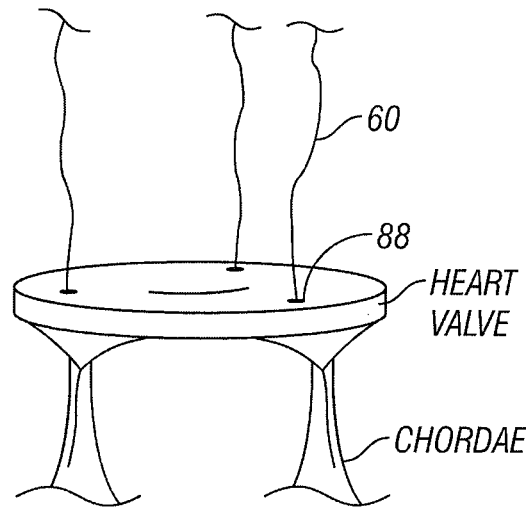
FIGS. 14A-14D illustrate the use of a support ring and sutures at a tissue site.

Referring now to FIG. 14A through 14D, a still further embodiment of the present invention will be described. As seen in FIG. 14A, sutures 60 may be secured to the tissues surrounding the heart valve at anchoring sites 88. The sutures may be secured in a variety of different methods including but not limited to passing sutures through the heart valve material to be looped through or knotted off using a knot pusher. The sutures may also be connected using anchoring devices as described in commonly assigned, copending U.S. Provisional Patent Application Ser. No. 60/388,250 filed Jun. 12, 2002.

Figure 14B:
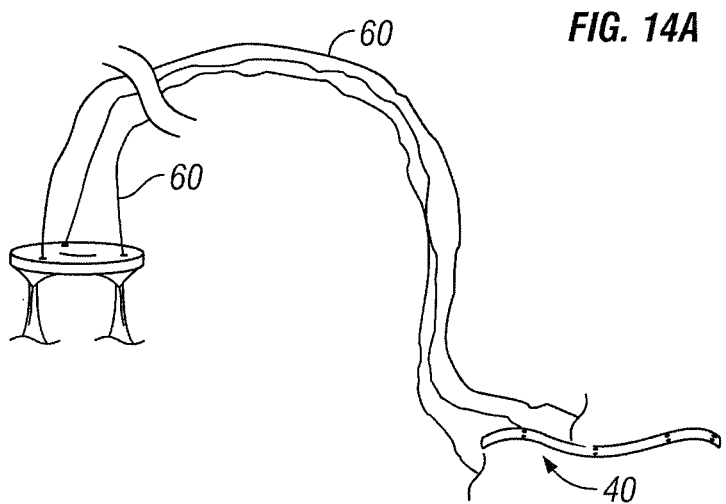
Figure 14C:
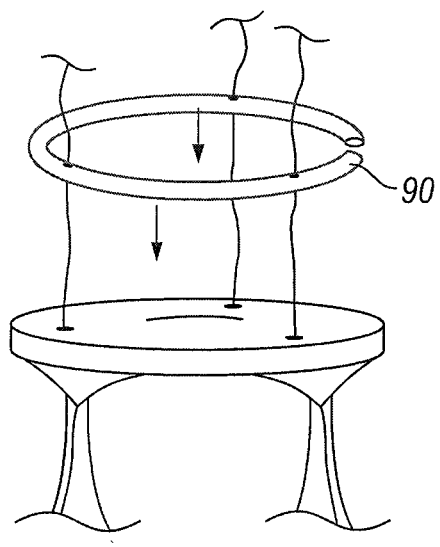
Figure 14D:
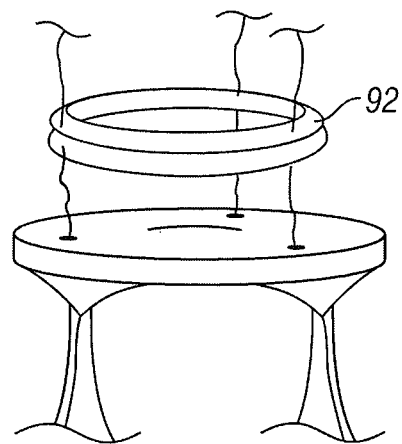

As seen in FIG. 14B, the sutures 60 may then act as guides to advance a slideable tissue supporting member 90 over the sutures to the tissues surrounding the heart valve. In one instance, the supporting member may be of similar size and shape to a conventional annuloplasty ring typically used to repair heart valves during open heart surgery. In one embodiment, the sutures 60 may be of sufficient length to extend from the attachment locations in the valve tissue to outside the body to allow for attachment to device 90. The device 90 may then be slidably advanced over the sutures to the target tissue. This advantageously allows for precise anchoring of the device 90 at the target site. As seen in FIG. 14C, the device 90 may have a single ring configuration that may be straightened or folded (in other embodiments) to be advanced through a guide catheter to the target site. Alternatively, the device 90 may be a continuous ring without a break, but foldable to be advanced through the guide catheter. As seen in FIG. 14D, a coil ring configuration device 92 may also be used, wherein both coils or rings of the device remain on the same side of the valve tissue. This may allow for additional attachment points on the device 92 or if the coils have varying diameters, different reshaping options based on different angles of the sutures to provide pulling or securing forces in different directions.

In the invention described, the ring may be advanced over the anchored sutures and advanced to the valve through a typical guide catheter. In such a manner, the entire procedure may be performed percutaneously, resulting in less trauma to the patient and providing improved valve function without the need for open heart surgery. After the ring is in position on the valve tissues, each of the locations where the sutures pass through the ring are fastened to the ring using the techniques previously described with clamps and/or knots. Alternatively, it may be possible to secure all of the sutures with a single clamp securing each of the sutures together, as shown in Figure, below.

Figure 15A:
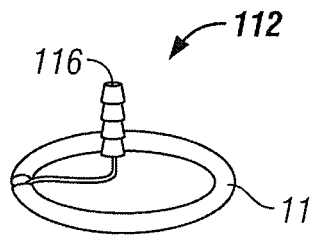
FIGS. 15A-20 show embodiments of the present invention using separable clamping portions.
Figure 15B:
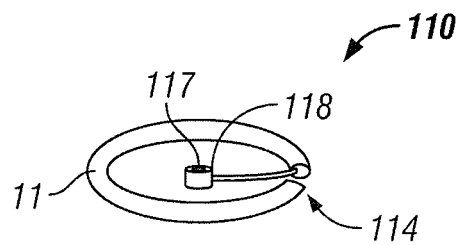

Referring now to FIGS. 15A and 15B, in another embodiment of this invention, the device 110 consists of two separate halves or clamp portions 112 and 114, each of which may provide support for the valve while maintaining a clamping force between them. Clamp portion 112 may have an annular support 113 or leaflet that supports the tissue. Clamp portion 114 may similarly have an annular support 115 or leaflet that supports the tissue. The two clamp portions 112 and 114 are connected to each other via a central adjustable fitting. In one embodiment, the central fitting consists of a barbed connector or spine 116 on one device part that mates to a matching insert 117 on the opposite part with a lumen 118.

Figure 16:
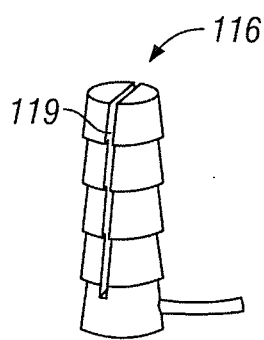

As seen in FIG. 16, the center spine 116 could be split, having a slot 119, to permit the outer diameter of the spine to be adjustable, allowing the distance between the two parts to be adjusted by the physician in-vivo, until the improved function of the heart valve has been observed.

Figure 17:
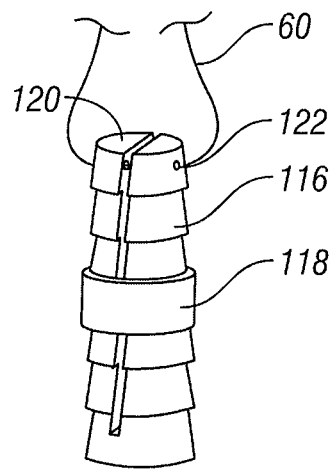
Figure 18:
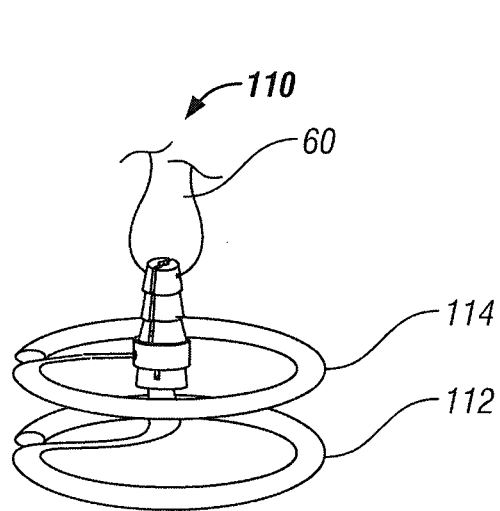

In a further preferred embodiment seen in FIG. 17, the distal end 120 of the center spine 116 may incorporate holes 122 on each half of the barbs. Through the holes 122 is a releasable suture or thread 60 that, when tension is applied, compresses the two halves of the spine 116 together, effectively decreasing its overall outer diameter. This permits the upper half of the device to be adjusted prior to release to allow for more distance between the two halves of the device and less clamping force on the valve area. The complete assembly, including the releasable suture, is illustrated in FIG. 18 (for illustrative purposes, the ring and clamp are shown as simple circular structures). In this manner, the clamping force on the valve and annular support device is entirely controlled by the physician prior to its release in the heart.

Figure 19:
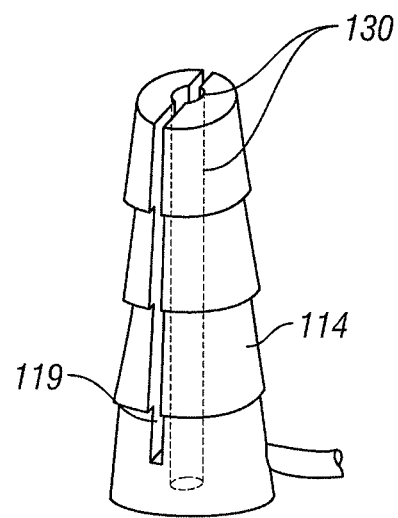

In a further embodiment of the present invention as seen in FIG. 19, the device 110 comprises a lumen 130 through the center spine 116. The lumen 130 provides a space through which a slideable and removable guide wire may be inserted for placement of the device. A matching lumen 118 on the mating half 114 of the device ensures that both pieces remain in the same axis when being delivered. Since both parts of the connector are maintained in axial alignment, securing the devices together is accomplished by pushing the two devices together.

Figure 20:
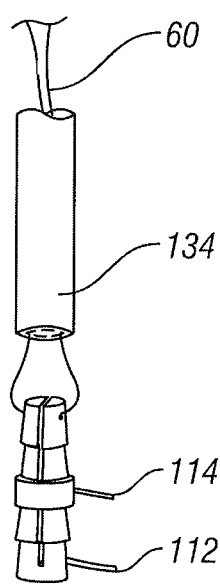

A pushing device 134 of FIG. 20, consisting of a tubular member, allows for tension to be placed on the releasable suture 60 without disrupting the location of the valve support device by holding the center spine in position while tension is applied to the suture. After the desired improvement in valve function has been obtained, the suture is removed by simply releasing one end of the suture and pulling on the other end until the entire suture has been removed from the body. Additionally, other release mechanisms include clamping jaws, screw threads, and other mechanical means, that are releasably connected to the support structure in order to maintain control over the device and to remove the structure from the body if improvement is not realized or for any other reason.

Again, each of the halves 112 and 114 of the device may be hollow allowing for them to be straightened over a mandrel or guide wire for delivery into the valve area. Upon delivery to the valve are, the device(s) are advanced off the removable mandrel/guide wire and they revert back to their pre-determined shape.

In addition to the various coil type annular support rings described above, other types of annuloplasty device may also be used in accordance to the present invention.

Figure 21:
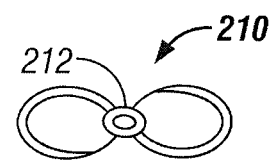
FIGS. 21-27D illustrate varying geometries of leaflet clamps for use with the present invention.
Figure 22:
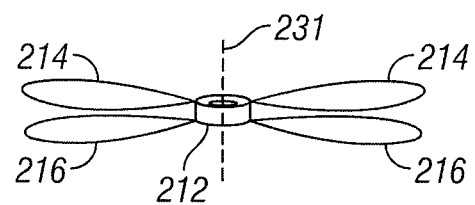

Referring now to FIGS. 21 and 22, in another embodiment of the present invention, a valve support structure 210 is delivered to the valve area via a guide catheter. The device 210 comprises of a central body 212, a first leaflet clamp 214 defining an upper compressive portion, and a second leaflet clamp 216 defining a lower compressive portion. The clamp 214 and clamp 216 may be positioned to engage the valve leaflet therebetween.

Figure 23:
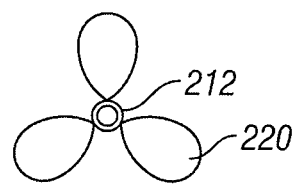

Referring now to FIG. 23, the number of leaflet clamp sets on the device may match the number of leaflets of the valve. For instance, the mitral valve device of this invention may have two sets of clamps. The tricuspid device design may, but is not required to have, three sets of leaflet clamps 220 as seen in FIG. 23. In either instance, the clamps are connected at a central location and radiate outwards towards the valve leaflets.

Figure 24:
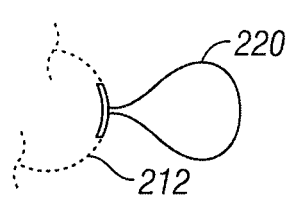
Figure 25:
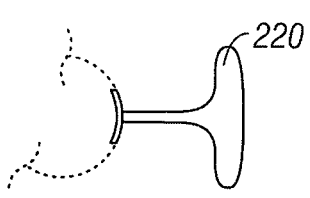
Figure 26:
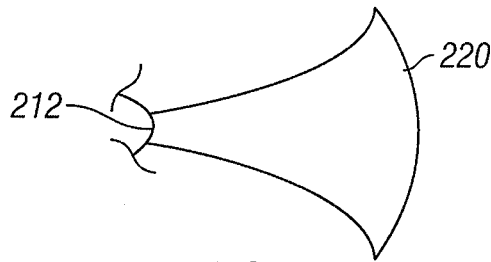

Each leaflet clamp 220 may have a different geometry, depending on the condition of the valve. For instance, if more support is desired at the outer edge of the leaflet, the clamp could have a larger diameter in that area. FIG. 24 shows a wire loop leaflet clamp 220 having a curved configuration where the wire extends radially outward and then returns to the central body 212. FIG. 25 shows an embodiment where the change in width is more pronounced as the wire loop reaches the outer radial portion of the clamp. FIG. 26 shows an embodiment having an oar or paddle configuration. It should be understood that a variety of different geometries may be used to support the leaflet clamps.

Figure 27A:
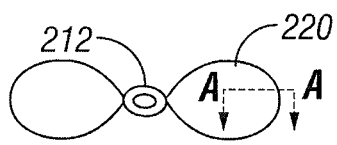
Figure 27B:
Figure 27C:

Referring now to FIGS. 27A-27C, the cross section of the clamp 220 may also have various geometries. For instance, it may be desirable to distribute the clamping force over a larger area, in which case a flattened cross section would be appropriate as seen in FIG. 27B. Alternatively, rounded cross sections may be used in areas where there may need to be increased force on the tissue surface as seen in FIG. 27C.

Figure 27D:
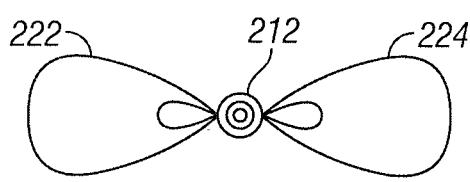

It can be appreciated that there may be any number of configurations for the clamps 214 and 216. For instance, if most of the support for the valve is needed at the area of the annular ring, the clamps may not provide any clamping force on the leaflets themselves, but would be of sufficient overall diameter and distance away from the central hub so as to provide support in the annular area of the valve. Conversely, if a percutaneous procedure yielding similar results to the "bow-tie" procedure is desired, the clamps may be of relatively small outer diameter. In this manner, only the leaflets would be clamped together more central to the device, effectively decreasing the movement of the leaflets, and providing a forced coaptation. Additionally, as seen in FIG. 27D, a combination of both annular support 222 and leaflet coaptation 224 could be achieved in the same device by providing multiple clamps of different diameters to support both the valve leaflets and the valve's annulus.

Figure 28:
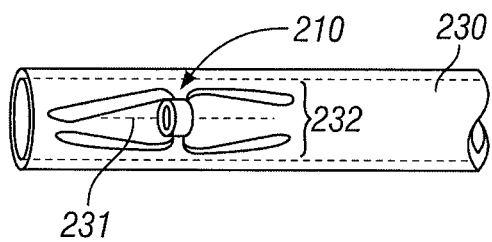
FIGS. 28-30 show the delivery of an apparatus according to the present invention with deflectable leaflet clamps.
Figure 29:
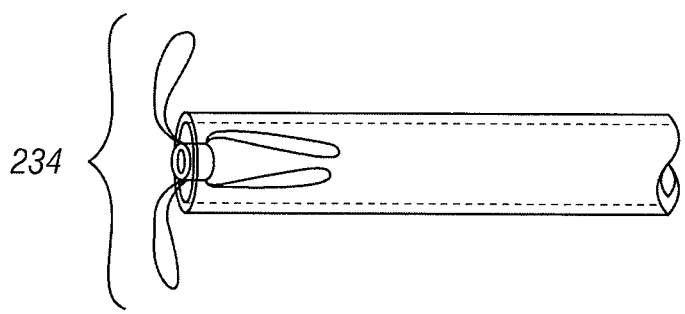
Figure 30:
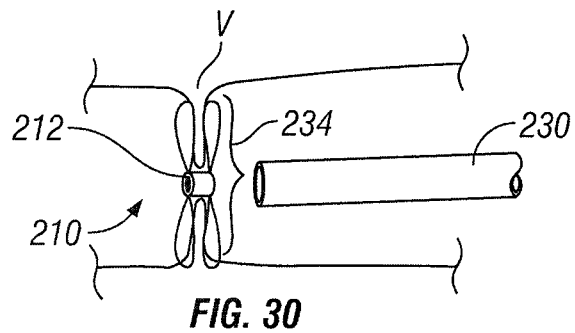

Referring now to FIGS. 28-30, delivery of the device 210 may be achieved through a guide catheter 230. Each of the leaflet clamps 214 and 216 may be made of a superelastic material such as, but not limited to, Nitinol, such that the leaflet clamps 214 and 216 can be folded up into the guide catheter to assume a folded configuration. As seen in FIG. 28, the leaflets clamps are deflected towards a longitudinal axis 231 of the central body to provide a reduced diameter 232 so that the device 210 will fit inside the guide catheter but still assume an expanded configuration with an extended diameter upon exiting the catheter.

As seen in FIGS. 29 and 30, upon release across the heart valve V, the leaflet clamps 214 and 216 return to their functioning state with the extended diameter 234. Alternatively, the device 210 may be made of any one of a number of shape memory alloys, allowing it to be delivered in a straight configuration through the guide catheter, and re-assuming its functioning form following the application of energy in the form of electrical, radio frequency, microwave, and such. In any case, the guide catheter is traversed across the target valve. At the desired location, the device is pushed out the distal end of the guide catheter and upon exiting the guide catheter as seen in FIG. 29, the distal leaflet clamp 214 assumes its clamping dimensions.

The guide catheter 230, still with the proximal leaflet clamps 216 inside in their folded configuration, is then retracted proximally across the valve opening where the remainder of the device 210 is delivered. The leaflet clamp 216 then extends to their preformed configuration with diameter 234, engaging or urging the valve leaflet against the opposing clamp 214 as seen in FIG. 30.

Figure 31:
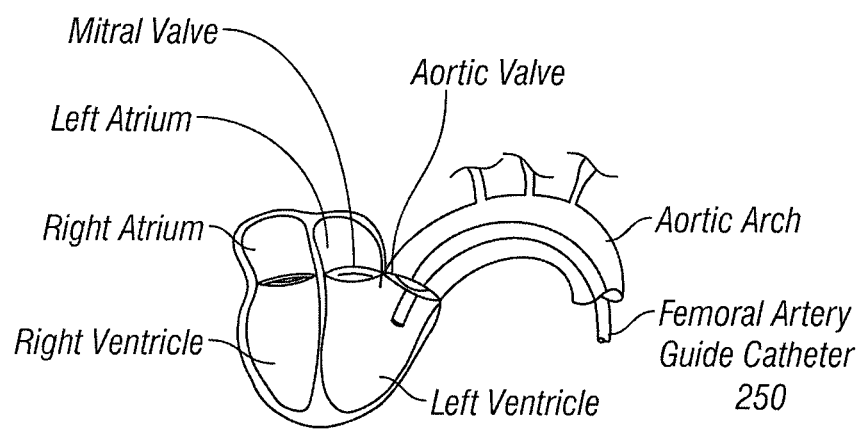
FIGS. 31-35 illustrate positioning of delivery devices to reach a treatment site in the heart.

Referring now to FIGS. 31-35, there are several ways the mitral valve can be accessed percutaneously to deliver the devices described herein, although it should be understood that the devices may be used during open heart surgery as well. As seen in FIG. 31, one route utilizes the femoral artery approach where the guide catheter 250 is threaded through the femoral artery in the groin and advanced retrograde against the flow of blood, over the aortic arch, through the aortic valve, into the left ventricle of the heart, and directed towards the mitral valve.

Figure 32:
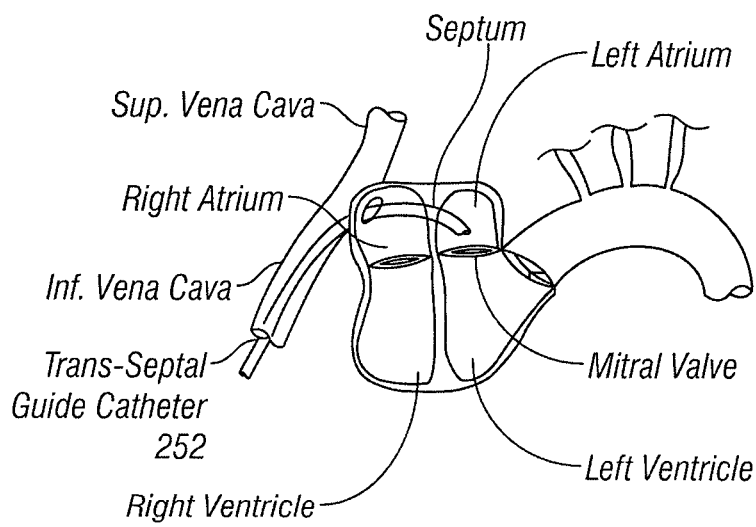

Referring now to FIG. 32, a second approach that may be used during percutaneous valvuloplasty procedures involves the venous approach to the heart. The guide catheter 252 is advanced through the vena cava into the right atrium of the heart and is directed across the atrial septum of the heart into the left atrium of the heart. This approach has been demonstrated to be well-tolerated by the body with few adverse events.

Figure 33:
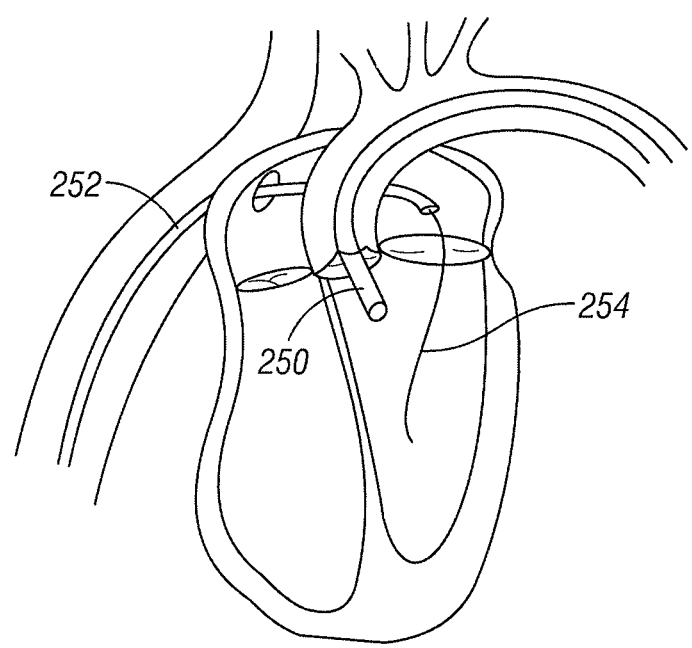
Figure 34:
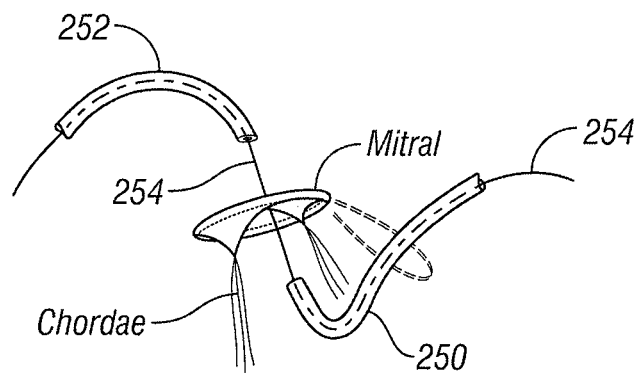

Referring now to FIG. 33, a further method for device placement is described herein that provides unique advantages for devices attempting to modify the performance of the mitral valve percutaneously. First, a trans-septal guide catheter is advanced through the atrial septum of the heart to the superior side of the mitral valve. An extra long guide wire 254, is then advanced through the guide catheter 252 and into the left ventricle. A second guide catheter 250 is advanced to the left ventricle of the heart via the arterial approach. A snare (not shown) may then be advanced through the arterial guide catheter 250 and captures the distal end of the trans-septal guide wire 254. The snare is retracted through the arterial guide catheter 250 where the distal end of the guide wire is captured and secured outside the body. In effect as shown in FIG. 34, the guide wire 254 provides a passage from either or both directions, arterial or venous, to the mitral valve of the heart.

Figure 35:
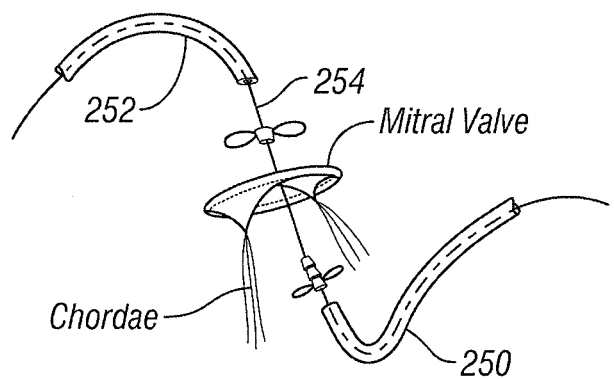

Referring now to FIG. 35, a support ring 112 when threaded over the guide wire from the arterial side need not even cross the mitral valve to provide support to the ventricular side of the valve. Similarly, a second support ring 114 forming device 110 when combined with ring 112, intended to provide support to the atrial side of the mitral valve also need not cross the valve when delivered via the trans-septal route. In this manner, the two halves of mitral valve device 110 can be delivered through the two guide catheters and meet up at the mitral valve. The guide wire 254 additionally ensures that the two mating parts of the device remain in axial alignment when assembled across the valve.

Figure 36:
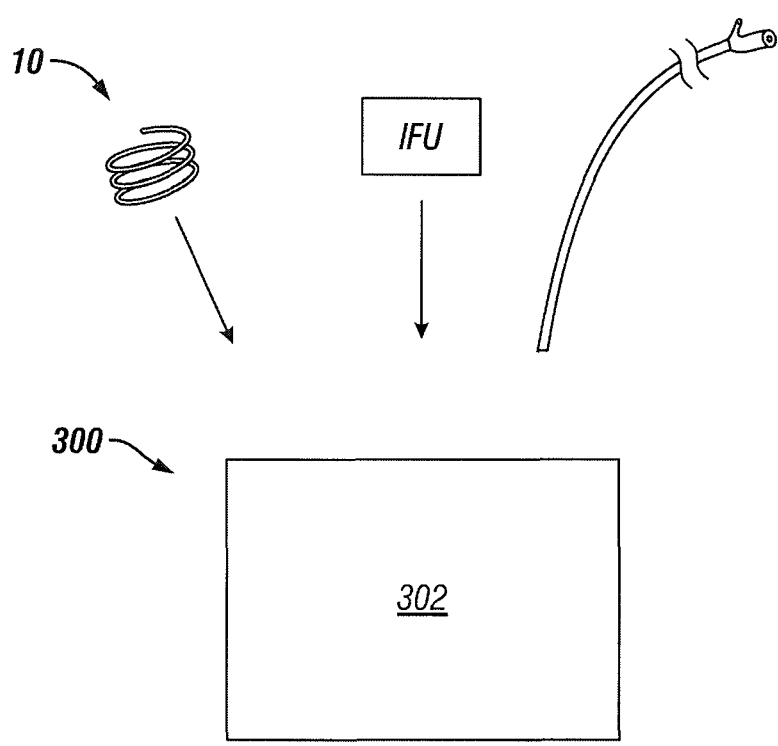
FIG. 36 shows a kit containing an annular support ring and accessories.

Referring now to FIG. 36, the device 10 or any of the other devices 110 or 210 as described herein, may be included in a kit 300 contained in a pouch or container 302. Instructions for use IFU are also contained in or attached to the container 302. The instructions provide a method for using device 10, a method for attaching device 10 to tissue, or instructions on how to deliver device 10 or similar device using a delivery device 20 such as a catheter or straightening mandrel that may also be contained in container 302. It should be understood that the kit 300 may include anchors and delivery devices 500, illustrated in FIGS. 78-80, in addition to or in place of devices 110 and 210.

Figure 37:
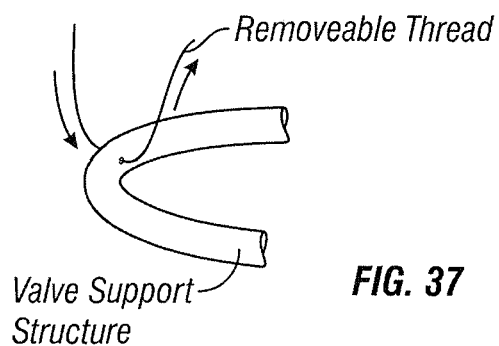
FIG. 37 shows a suture coupled to a support member.

FIG. 37 shows that sutures or threads may be removed from the angioplasty ring.

Figure 38:
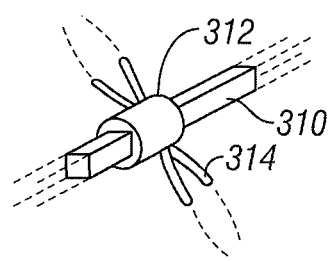
FIGS. 38-39 show clamps for used with shaped guide wires.
Figure 39:
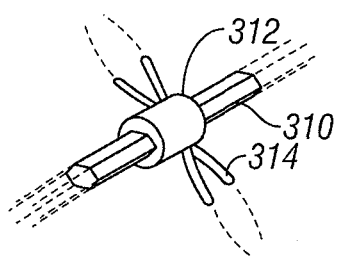

Referring now to FIGS. 38 and 39, it can be appreciated that the cross section of the guide wire 310 may be shaped to ensure the proper orientation of the two device halves. In this manner, torqueing of the guide wire 310 with the device 312 slideably attached also orients the device 312 loaded on the guide wire. The steerability of the guide wire 310 and the valve device may help in the proper orientation of the clamps 314 of the device onto the leaflets of the valve.

Figure 40:
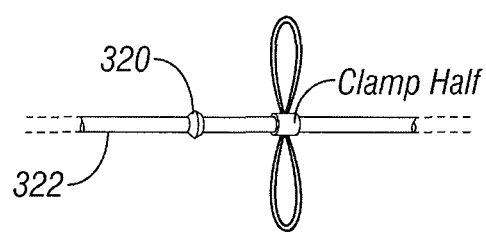
FIGS. 40-43 show delivery of anchors into tissue.

Referring now to FIG. 40, additionally in a still further embodiment, an integral bump 320 on the guide wire 322 may aid in providing additional force to connect the valve support device or to seat it against the tissues of the heart valve. The bump 320 on the guide wire 322 provides enough interference with the device so that as the guide wire is advanced or retracted, it pulls the device along with it.

Figure 41:
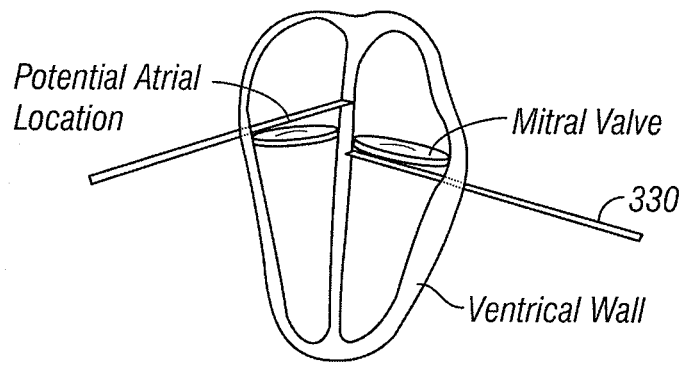

Referring now to FIG. 41, additional placement techniques for the device according to the present invention include using thoroscopic techniques to place the devices. During this procedure, a small port(s) is usually used to access the heart tissues. The port is typically placed between the ribs using laparoscopic methods. A metallic tube or guide catheter is then advanced up to the heart tissues to gain access to the major vessels and the exterior of the heart muscle. The technique that may be particularly useful is where the anchor is inserted through the heart muscle at or near the level of the damaged valve.

Figure 42:
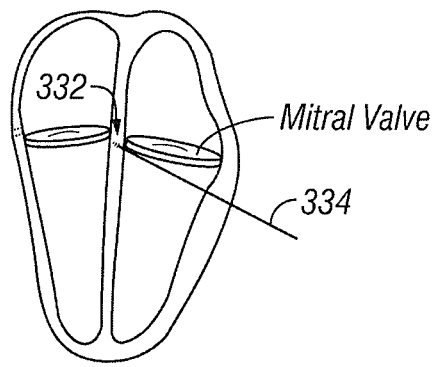
Figure 43:
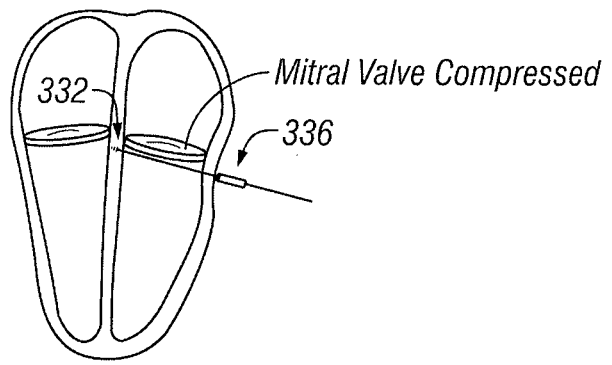
Figure 44:
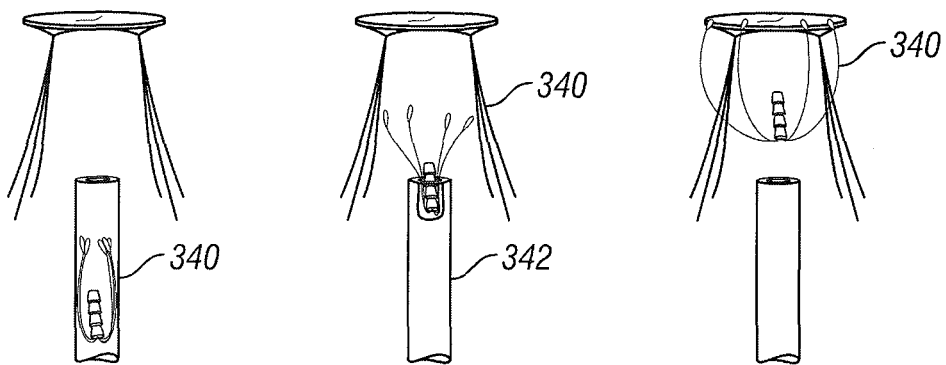
FIGS. 44-52 show additional techniques for delivering support devices to tissue.

The hypo delivery tube 330 pierces through the heart muscle into the atrium or the ventricle near the valve. The needle is then further advanced across the interior of the heart to the opposite side of the valve where it again pierces through the heart wall. The anchor 332 is then deposited on or in the opposite side of the heart and the suture 334 left behind in the path of the needle as the hypo is retracted from the heart muscle as seen in FIG. 42.

A clamp 336 may then be advanced down the suture to the initial side of the piercing. As the clamp 336 is further advanced, the sides of the heart are drawn closer to each other, assisting the valve leaflets in proper coaptation and improved function.

It should be understood that although a suture is described, a steel rod or similar support structure may be used to transverse through the heart muscle. The main concept is that opposite sides of the valve are brought closer to one another by an external force on the heart muscle. Alternatively, if valvular stenosis is being treated, the valve can be forced open in a similar manner. In this manner, the spanning structure is rigid since it is under compression from the force of the heart muscle on the spanning rod.

Yet another embodiment of the present invention comprises the ventricular half of the annular support device having struts 340 instead of a ring or clip-like structure. The struts 340 are designed to atraumatically navigate through the chordae tendonae in the ventricle of the heart. During advancement through the guide catheter 342, the legs are extended distally. Upon exiting from the guide catheter, the legs 340 begin to spread outwards from the tip of the guide catheter towards the circumference of the valve. During their advancement, the legs gently push aside the chordae, if any, in their pathway.

Figure 45:
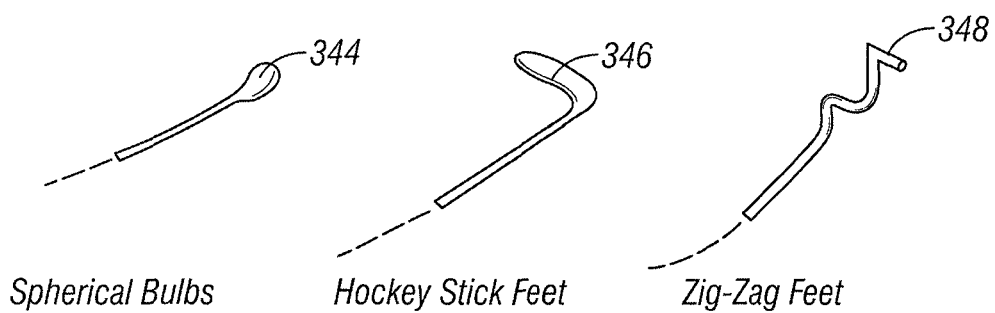

The ends of the legs or struts 340 may be shaped in any of a number of ways to allow for either more surface area on the ventricular side of the valve or to advance through the chordae easier. For instance as seen in FIG. 45, small spherical bulbs 344 on the ends of the legs provide a smooth leading edge for the legs with little risk of snagging a chord as the legs advance through the chordae. After traversing through the chordae, the landing pads on the legs secure themselves on the ventricular side of the mitral valve, either at the leaflet or directly onto the annulus of the valve. In other embodiments, the ends of struts 340 may have a hockey feet 346 configuration or a zig-zag 348 configuration.

Figure 46:
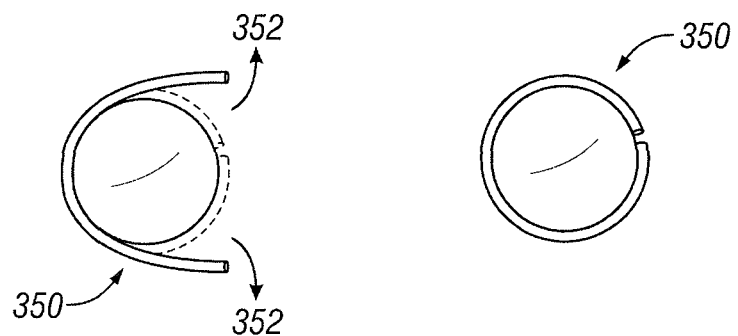

Referring now to FIG. 46, another aspect of modifying the heart valve for improved function includes devices that treat valvular stenosis. These devices provide expansive forces to the valvular annulus in order to increase the open area of the valve through which blood flows. One such device 350 utilizes an outward expansive force to apply pressure to the annular area of the heart valve as indicated by arrows 352. The coil is delivered through a standard guide catheter and, upon exiting the distal end of the guide catheter, the device assumes a predetermined generally ring-shaped structure that presses itself against the heart wall, either immediately superior (atrial side) or inferior (ventricular side) of the valve.

Alternatively, the device may be generally cylindrical in shape, and upon exiting the guide catheter, it assumes a larger diameter that presses against the heart wall, either immediately superior (atrial side) or inferior (ventricular side) of the valve. Furthermore, the device may be hollow, allowing for it to be straightened for delivery over a removable straightening mandrel or guide wire. Upon removal of the mandrel or guide wire, the ring reverts back to its larger diameter pre-determined shape and provides a force on the interior of the heart wall, thus modifying the function of the heart valve in its vicinity.

Figure 47:
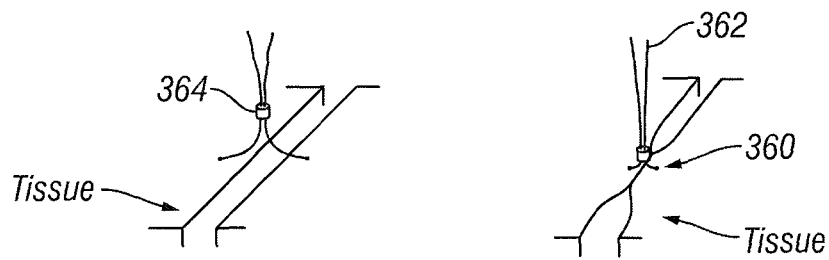

Referring now to FIG. 47, another aspect of this invention provides devices, methods and systems for suturing and repairing tissues of the body. Specifically, tissues can be "cinched" together, or brought into closer proximity to one another, using the devices described herein. In one embodiment of this invention, anchors 360 are attached to the tissues to be cinched. Attached to the anchors 360 are sutures 362. A slideable clamp is attached to the sutures. As the clamp 364 is slid closer to the anchor points, the tissues are brought closer together. When the desired position of the tissues has been achieved, the clamp 364 is set in position and the excess suture material from each anchor point is severed and removed.

Figure 48:
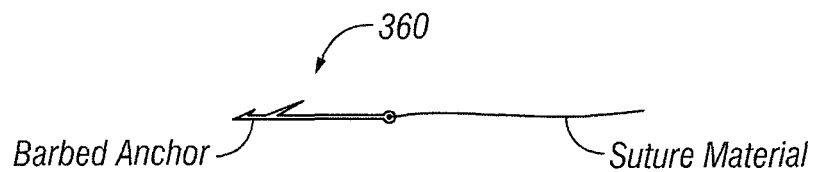

The anchors 360 may be of any of a number of configurations. For instance as seen in FIG. 48, a spear-like design would enable the anchor to penetrate tissue with the barb providing adequate resistance to the tension applied to the suture during the cinching process.

Figure 49:
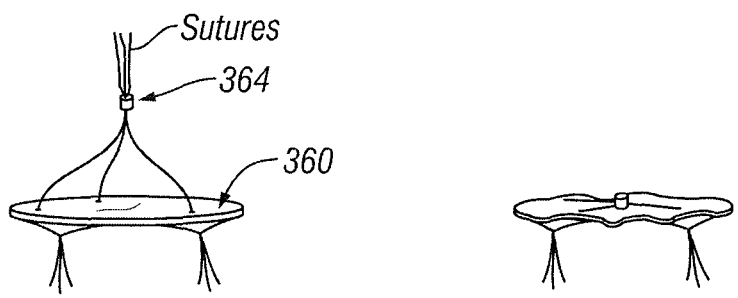

Referring now to FIG. 49, in the case of repairing a heart valve, two or more anchor 360 may be placed in any of the tissues surrounding the valve leaflets, including the leaflets themselves. Following the proper placement of the anchors and attached sutures 362, the slideable clamp 364 is advanced over the sutures and adjusted to provide adequate tension on the anchor points on the valve to provide improved coaptation of the valve leaflets. When adequate improvement in the function of the valve has been obtained and verified, the clamp is set in place and the excess suture material cut and removed.

Figure 50:
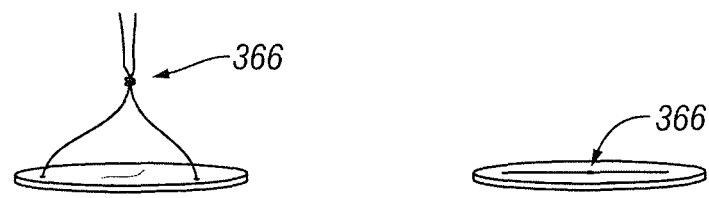

For illustrative purposes, the clamp 364 is shown as a tubular member, however, simple means of securing the tension on the sutures may be accomplished by any one of several means. For instance as seen in FIG. 50, a simple knot 366 tied in the proximal end of the sutures and advanced towards the valve by a knot pusher, would provide adequate means for securing the tension in the sutures.

Figure 51:
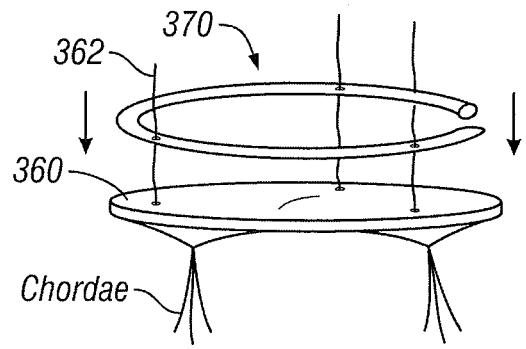

Referring now to FIG. 51, in another embodiment, one or more anchors 360 and sutures 362 are secured to the tissues surrounding the heart valve. The sutures then act as guides to advance a slideable tissue supporting member 370 over the sutures 362 to the tissues surrounding the heart valve. In one instance, the supporting member 370 may be of similar size and shape to a conventional annuloplasty ring used to repair heart valves during open heart surgery.

Figure 52:
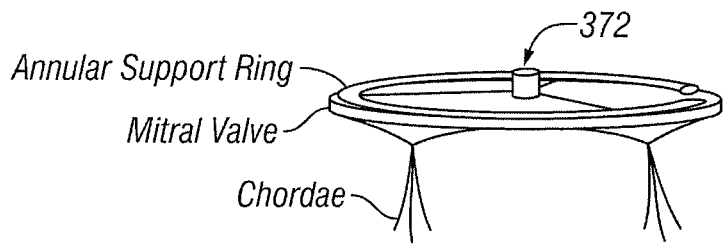

In the invention described, the support member 370 may be advanced over the anchored sutures and advanced to the valve through a typical guide catheter. In such a manner, the entire procedure may be performed percutaneously, resulting in less trauma to the patient and providing improved valve function without the need for open heart surgery. After the support member 370 is in position on the valve tissues, each of the locations where the sutures pass through the ring are fastened to the ring using the techniques previously described with clamps and/or knots. Alternatively, it may be possible to secure all of the sutures with a single clamp 372 securing each of the sutures together, as shown in FIG. 52.

In one embodiment, the support member material may be made porous in order to promote endothelialization of the member 370 around the valve. A more secure device may aid in the support the implantable ring provides to the valve tissues. Suitable materials for the ring include nitinol, ceramics, and plastic polymers. Additionally the materials used may elude drugs that may assist in the promotion of endothelialization. Alternatively, the support member 370 may be surrounded by materials such as polyester that promotes tissue ingrowth and endothelialization of the device.

Figure 53:
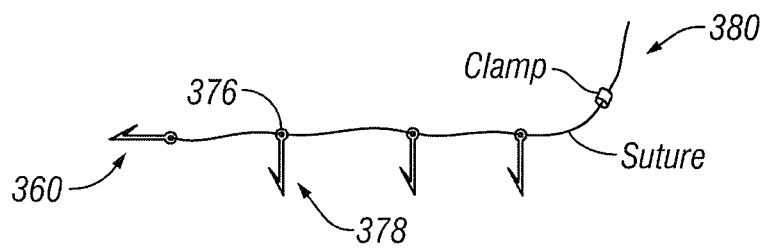
FIGS. 53-60 show various anchor embodiments according to the present invention.

Referring now to FIG. 53, in another aspect of this invention, the anchors 360 incorporate a loop 376 of material or a lumen through which a suture may slide 380. The first anchor 360 placed typically has a non-slideable suture attached. Once the first anchor point has been secured in the desired location, subsequent anchors 378 are slid over the primary suture and secured to the tissues of the valve.

As tension is applied to the primary suture 380, each of the anchor points are brought into closer proximity to one another (see FIG. 57), resulting in improved coaptation of the valve leaflets and improvement in the function of the heart valve. Following the final anchor attachment to the tissues, a single clamp 372 or knot is advanced to the location of the final anchor and secured in place following verification of improved function. Valve function may be verified by any one of many suitable means including, but not limited to, echocardiography, angiography, magnetic resonance imaging, etc.

Figure 54:
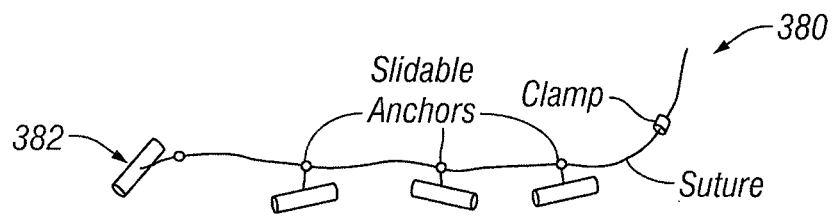

Referring now to FIG. 54, the anchors may be of any suitable design to provide adequate prevention of dislodgement when the primary suture is place in tension. An alternative embodiment to the barbed spear is a "T" bar design anchor 382 is used in various alternative procedures such as in gastrostomy placement.

Figure 55:
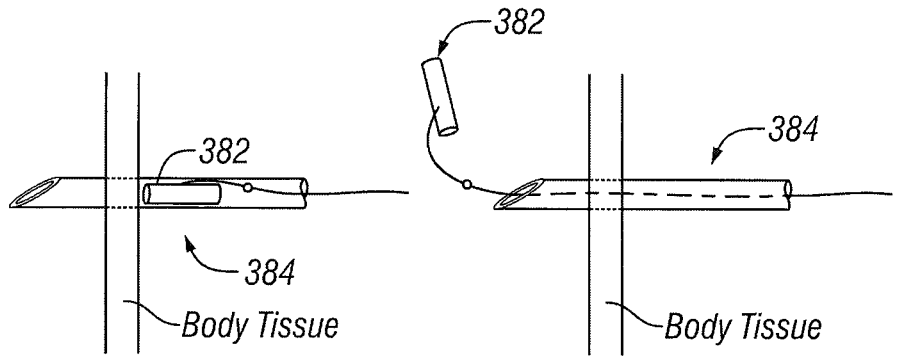
Figure 56:
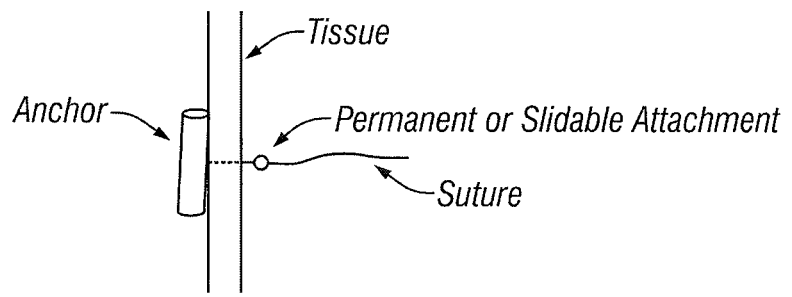

Referring now to FIG. 55, in one embodiment, the "T" bar 382 is placed via a hypodermic needle or tube 384. The needle 384 punctures through the tissues to be cinched and then the "T" bar 382 is deposited on the opposite side by a simple mandrel or "T" bar pusher. The needle is then retracted leaving the "T" bar anchor securely fastened to the opposite side of the tissue as seen in FIG. 56.

Figure 57:
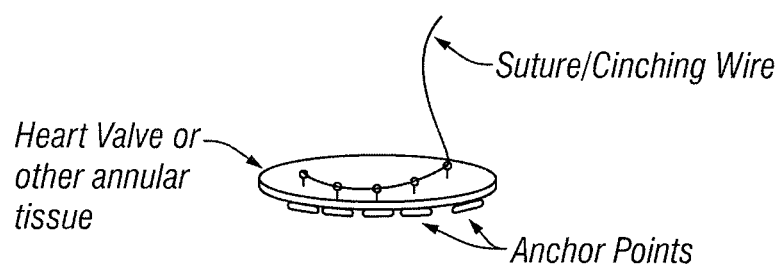

Subsequent anchors are added by removing the "T" bar pusher from the catheter, loading a slideable anchor over the primary suture, and advancing the anchor through the hypo tube to the next desired position. The target tissue is then pierced by the "T" bar delivery hypo tube, the "T" bar anchor pushed out the end of the hypo, and the hypo retracted, leaving the "T" and primary suture attached to the anchor point. Additional anchors may be placed in a similar fashion as seen in FIG. 57.

Figure 58:
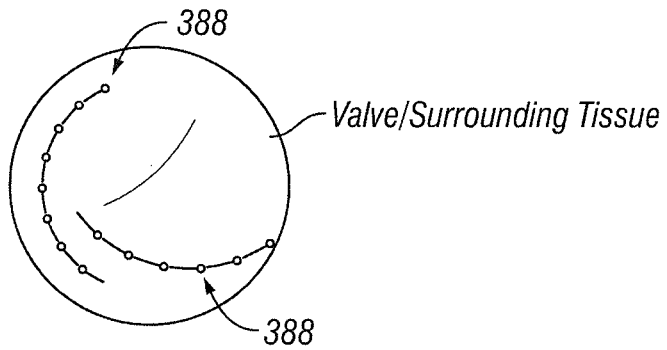

Referring now to FIG. 58, in this manner, multiple anchor points 388 may be placed around a heart valve or other tissue that is in need of support. As tension is applied to the primary suture, the anchors provide the points at which constriction occurs and the overall diameter of the valve annulus is reduced much like the use of a belt through the belt loops on a typical pair of trousers. By this method, several series of anchors and sutures may be placed that specifically provides constriction on only those areas of the valve that may be in need of cinching.

It is important to note that although the repair of the heart valve is described, this device and technique may also be very useful in the non-surgical repair of other tissues within the body. For instance, Gastrointestinal Reflux Disease may be treated by using these techniques on the sphincter between the esophagus and the stomach. By effectively decreasing the overall diameter of the excess opening typical of this disease, normal function may be restored. Additionally, urinary incontinence may be treated using similar techniques and devices on the sphincter between the bladder and the urethra. In these instances and others, surgery may be significantly reduced or eliminated, thus sparing the patient from the risks of surgery and the necessary recovery from such trauma.

Figure 59:
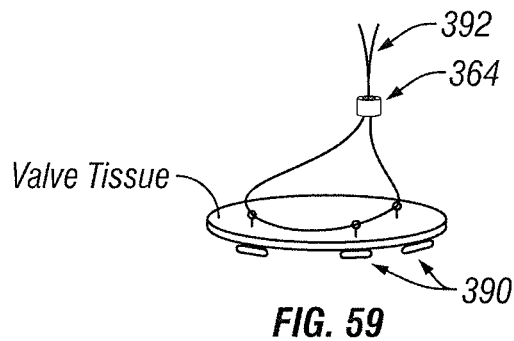

Referring now to FIG. 59, another technique that can be used is where each of the anchors 390 are slidable with no primary anchor. Instead of the initial anchor having a permanent suture attached, a single (or multiple strands) suture 392 is threaded through a hoop on each of the anchors 390 with both ends of the suture exiting through the delivery guide catheter. The tissue is then cinched together by advancing a knot or clamping device 364 using the two ends of the suture as the point where the tension is applied.

Figure 60:
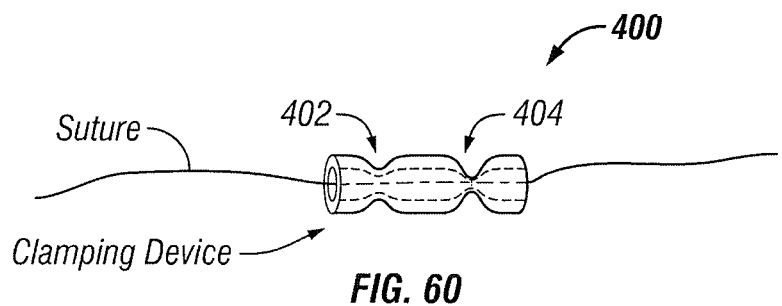

Referring now to FIG. 60, if a clamp 364 is advanced towards the anchors, the clamp itself may have a means to both clamp the ends of the suture together and simultaneously cut the excess suture material from the site. FIG. 60 shows a clamp 400 with a crimping area 402 and a cutting area 404.

Another method is where each of the anchors has non-slidable sutures permanently attached. In this instance, all of the ends of the sutures can be pulled together, and tied or clamped with a single knot or clamping device.

Figure 61:
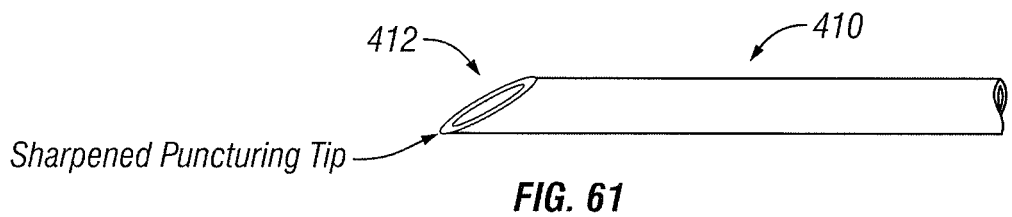
FIGS. 61-73 show various anchor and delivery devices for use in piercing tissue.

Referring now to FIG. 61, the hypodermic delivery tubing 410 for the "T" bar anchors or similar anchors may be of any number of suitable configurations to deliver the anchors. In one embodiment, the tubing 410 employs a simple sharpened needle tip 412 to puncture through the valve, leaflets, and/or the heart tissues surrounding the valve. The application of forward pressure on the tubing provides sufficient force for the tubing 410 to pierce the tissues and deliver the anchor to the opposite side of the heart structure.

Figure 62:
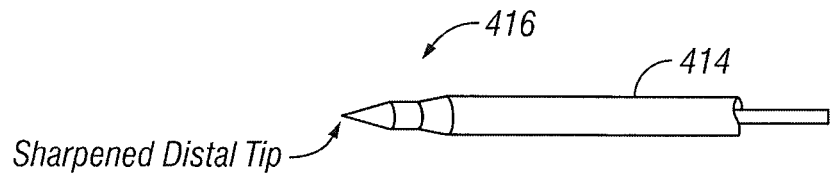

Referring now to FIG. 62, in another embodiment, the tubing 414 has a sharpened inner removable piercing obturator 416 that punctures through the heart tissues. After the tubing is through the tissues, the obturator is removed, allowing the anchor to be passed through the hypo tubing to the heart tissues.

Figure 63:
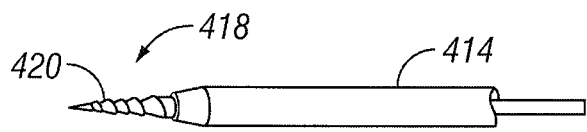

Referring now to FIG. 63, in another embodiment, the obturator tip 418 has self-tapping threads 420 on its distal end. Torqueing of the obturator screws the delivery hypo into the heart tissues. After the hypo 414 has been delivered to the desired location, the obturator is removed, allowing the anchor to be passed through the hypo tubing.

Figure 64:
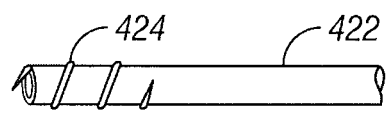

Referring now to FIG. 64, in another embodiment, the hypo tube 422 has threads 424 on its surface to permit the engagement of the hypo tube 422 with very little force. Torqueing of the hypo tube 422 screws the tubing into the heart tissues without requiring additional forward force on the tubing. In some cases, it does not require forward force greater than that used with a sharpened hypo tube. Once through the tissue, anchors may be advanced through the hypo 422 to their desired position.

Figure 65:
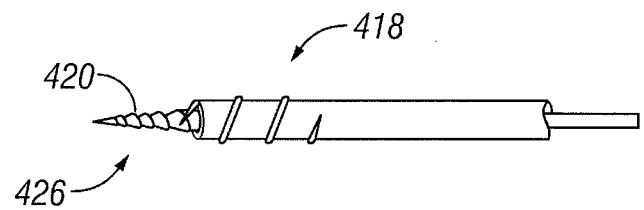

Referring now to FIG. 65, another embodiment utilizes self-tapping threads 420 on both the inner cannula 426 and the outer delivery hypo tube 428, preventing the possibility for coring of the tissue with the hypo tubing alone.

Figure 66:
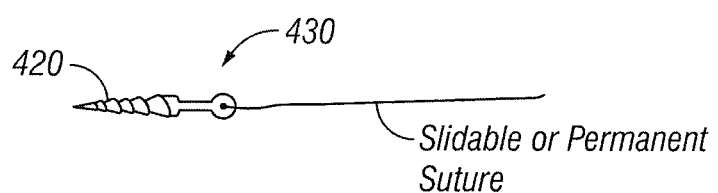

Referring now to FIG. 66, in yet another embodiment, the anchor 430 itself employs self-tapping threads 420 to engage the tissue and advance itself to the opposite side of the targeted tissue.

Figure 67:
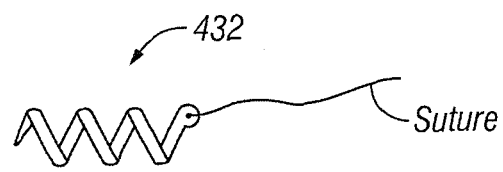

Referring now to FIG. 67, alternatively, the anchor 432 may be a simple self-tapping thread or a helix of sharpened wire similar to the distal tip on an active-fixation pacemaker lead that is secured to the heart tissue by torqueing through the tissue.

Figure 68:
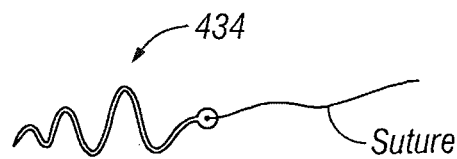

Referring now to FIG. 68, one possible improvement on the helical anchor 434 is that the helix may be of variable radii. For instance, the initial distal engaging winds of the helix may be of relatively small diameter, increasing in diameter proximally.

Figure 69:
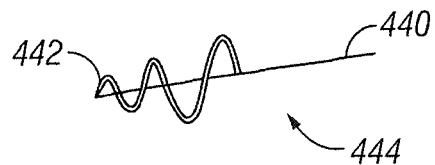

Referring now to FIG. 69, in this instance, additional anchoring force is provided, allowing for a more secure attachment. Additionally, the suture material 440 may be attached to the distal end 442 of the helix such that as more force is applied to the anchor by the suture, the anchor 444 tends to collapse upon itself, further providing additional support to the tissues in which it is attached.

Figure 70:
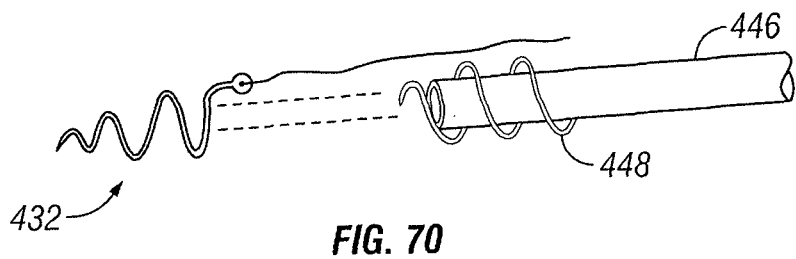

Referring now to FIG. 70, delivery of the anchor 432 is accomplished by securing the anchor 432 to a releasable delivery shaft 446. In one method of delivery, the anchor 432 is secured to the heart tissue by clockwise motion. Engaging threads 448 on the delivery shaft 446 allows clockwise rotation of the anchor for securement. Counterclockwise rotation of the delivery shaft 446 disengages the anchor 432 from the threads 448 on the delivery shaft. The delivery shaft is then removed from the guide catheter, leaving the anchor firmly secured within the heart tissue.

Figure 71:
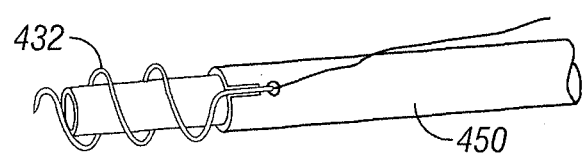

Referring now to FIG. 71 in another embodiment, the distal end of the guide catheter 450 releasably locks or engages at least a portion of the anchor 432. The anchor 432 is delivered with the engaging portion of the guide catheter retracted, and following delivery of the anchor, the guide is then advanced up to the anchor point to engage a portion of the anchor. By rotating the delivery shaft 450, the anchor is held in place, while the delivery shaft disengages. The guide catheter is then retracted from the anchor, leaving the anchor secured to the tissue.

Figure 72:
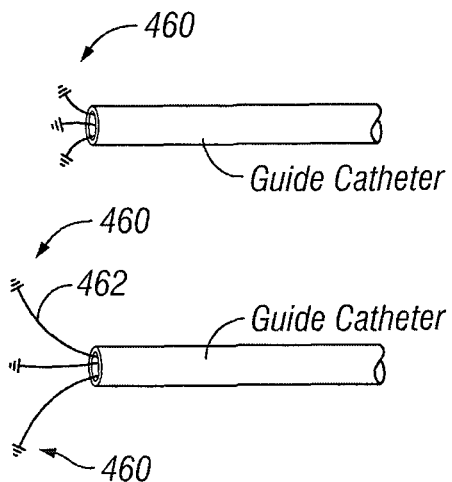

Referring now to FIG. 72, another method of delivery for the anchors is the simultaneous deployment of multiple anchors 460 at a time. In this manner, the delivery shafts 462 for two or more anchors are deployed at a variable distance apart. For instance, the ends of the delivery shafts 462 may be pre-shaped into a curved geometry such that as they exit the guide catheter, they progressively move further apart from each other.

Figure 73:
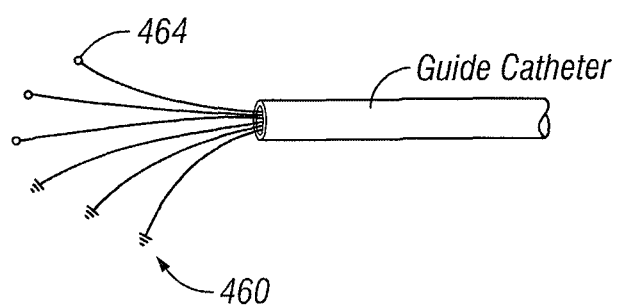

Referring now to FIG. 73, the more the delivery shafts 462 are advanced out the guide catheter, the greater the distance between the anchors 460. In this manner, several anchors 460 can be delivered in a pre-determined configuration at a pre-determined diameter away from the guide catheter. This eliminates the need to individually place each anchor at a desired location. Each projection outward from the guide catheter tip need not contain an anchor. In other words, one or more additional projections 464 may be used to center the device within the lumen of an artery or within the valvular tissue such that the anchors being delivered are oriented in the desired directions.

The anchor(s) may be porous in order to promote the endothelialization or encapsulation of the anchor in the tissue to obtain a more secure, long-term hold in the valve tissue. Suitable materials include ceramics, nitinol, elgiloy, stainless steel and the like. Alternatively, various polymers may be used that may or may not elude drugs to further promote endothelialization of the heart tissues into and around the anchors and/or the various other devices and inventions described herein. Additionally, the device may be used to close tubular organs, punctures or vessels from inside the tissues. In one instance, the fallopian tubes of a woman may be closed for permanent birth control. The device is threaded through a fallopian tube access catheter trans-cervically to the interior of the fallopian tube. One or more anchors may be delivered through the wall of the fallopian tube from the inside. The anchors are then secured to the exterior of the tubal wall and cinched together to close the tube. A clamp or knot that provides closure force is advanced to the site and secures the individual suture leads together. Again, the sutures may be fibered, stranded or bundled in order to facilitate tissue ingrowth and a more permanent occlusion of the fallopian tube. In this same fashion other organs, tissues and body passageways may be closed from the inside in order to effect the desired therapy or treatment.

Figure 74:
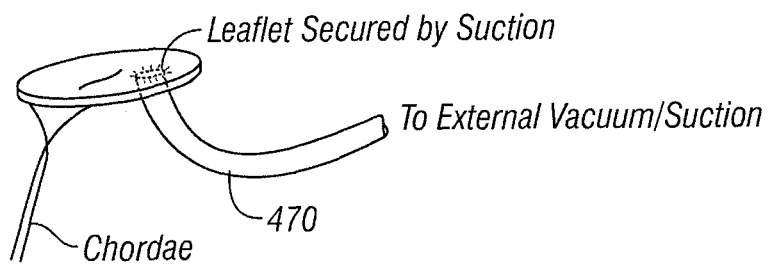
FIGS. 74-77 show additional uses of embodiments of the present invention.

Referring now to FIG. 74, another aspect to the delivery of the anchors is in providing a means for the guide catheter to grip or hold the tissues in close proximity to the distal end of the guide catheter. One such means is the provision for a simple vacuum to be placed on the proximal end of the lumen of the guide catheter 470. As the tip of the guide comes close to a soft tissue, the tissues are sucked closer to the guide catheter tip and held in place by the suction.

This vacuum device, the guide catheter 470 with an attached or detachable vacuum source, may also be particularly useful in the fixation of the stomach wall prior to percutaneous gastrostomy placement.

Figure 75:
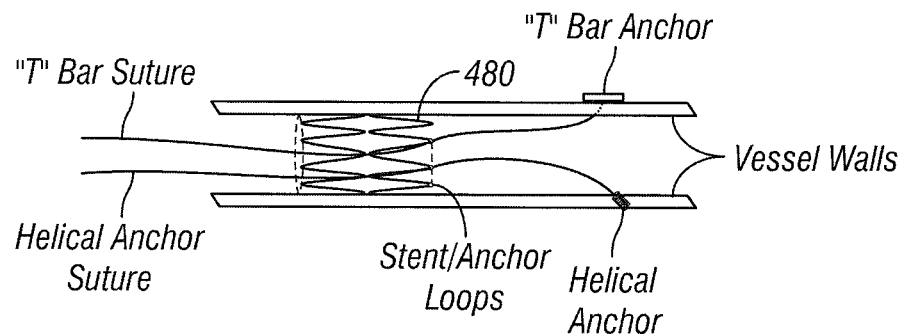

Referring now to FIG. 75, it is important to note that the anchors 460 may provide a means to improve the function of the heart valve alone, they may also be used to provide an anchoring means for various other devices used in the interventional treatment of cardiovascular diseases. For instance, although providing a means to secure the percutaneous annuloplasty rings described earlier, they may also be used to secure or affix a stent 480, or stent-graft to a vessel wall. In this application, first the anchors are delivered and secured to the desired tissue, such as the abdominal aortic vessel wall. The sutures on the anchors are threaded through loops such that the stent device can slide over the sutures. The stent is then advanced to the anchoring site. Knots or clamps are then advanced up to the stent so that the stent is then secured to the vessel wall at each of the anchor points.

Figure 76:
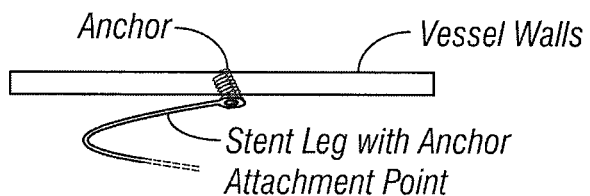

Alternatively, the anchors may be added after the stent has been delivered. The stent has specific points of attachment through which the anchors are delivered into the vessel wall. In this manner, the need for any suture material is completely avoided as seen in FIG. 76.

Figure 77:
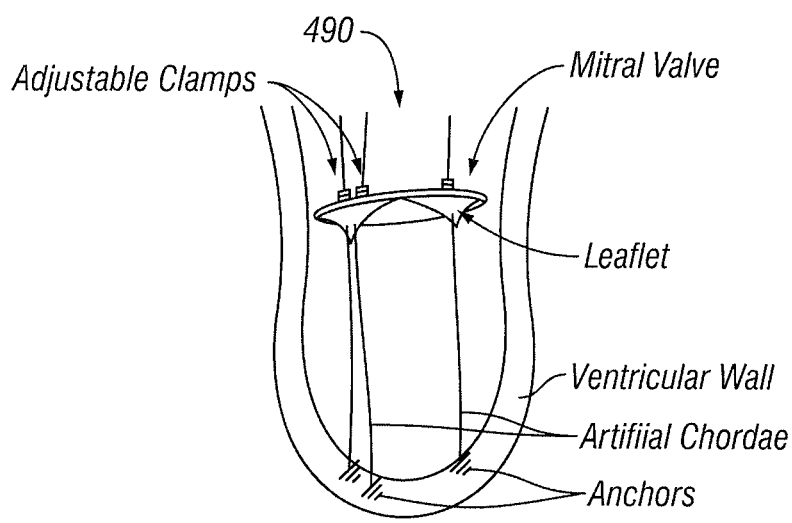

Referring now to FIG. 77, another aspect of this invention is an artificial valve 490 to replace a destroyed natural valve within the body. The natural valve may be one of the heart such as the mitral or aortic valves. Alternatively, the valve may be used in the legs of a patient with venous insufficiency. By providing improved fluid dynamics over the patient's natural valve(s), pooling of blood in the legs, typical in this disease, is minimized. The valve device 490 includes the valve itself, as well as an outer expandable support structure that secures the valve within a desired segment of blood vessel. The valve 490 may be made from materials typical of cardiac valves, such as carbon, silicone, nitinol and the like. Alternatively, the valve of this invention may be a tissue valve from a donor host, similar to porcine or bovine valves used for cardiac valve replacement. The valve may be processed venous valves from these animals, or they may be made from a valve structure that is temporarily grown within the living tissues of a host animal.

Yet another aspect of this invention provides a means for repairing the chordae tendonae that connect the leaflets of the mitral valve to the ventricular wall. In this device, the anchor is directed through the leaflet of the valve from the atrial side of the heart and placed within the ventricular wall. The leaflet is held in place by a knot or a clamp secured to the atrial side of the leaflet onto the suture attached to the anchor. Several sutures may be place in each of the leaflets in order to prevent prolapse during systole of the heart.

Figure 78:
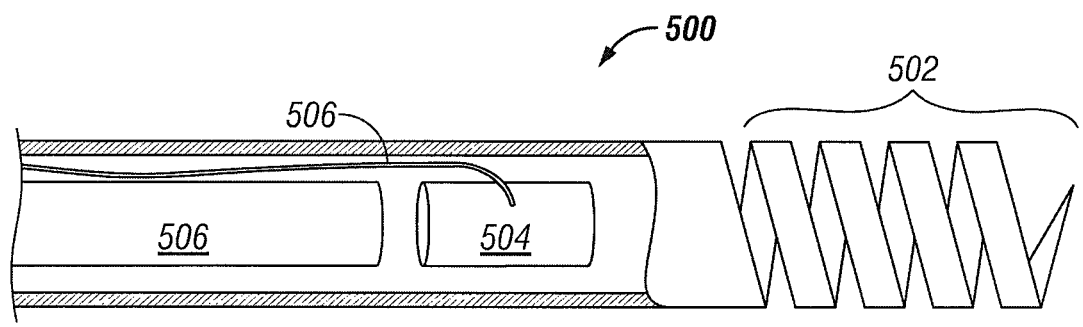
FIGS. 78-86 show still further embodiments of delivery devices and anchors according to the present invention.

Referring now to FIG. 78, a still further embodiment of a tube 500 for engagement of the tube 500 into tissue with reduced forward force. Torqueing of the tube 500 screws the tubing into the tissues through the cutting action of the helically cut distal portion 502 of the tube 500. Although not limited to the following, the cutting distal portion 502 may be formed by laser cutting or otherwise cutting a tube to remove material and form the structure shown. Other patterns may also be cut in the tube so long as they permit the tube to be advanced into tissue via torquing of the tube 500. Once through the tissue, anchors 504 may be advanced through the tube 500 to their desired position. In some embodiments, a pusher 506 may be used. In some embodiments, the anchor 504 may have a diameter substantially similar to that of the inner diameter of the tube 500 but allowing for unimpeded delivery of the anchor through the tube. A suture 506 may be coupled to the anchor 504.

Figure 79:
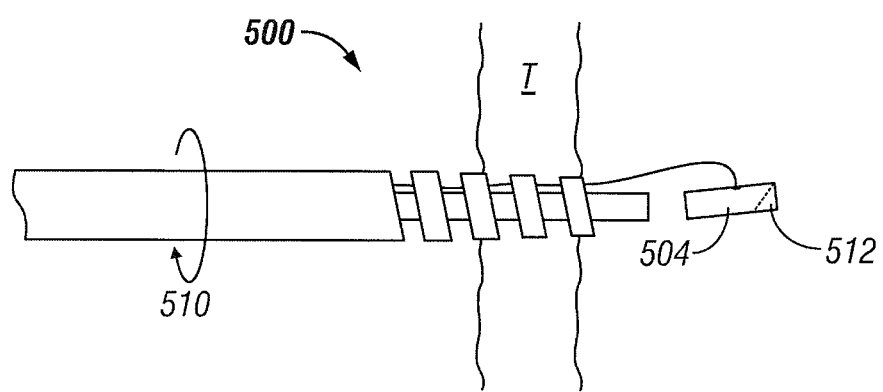

Referring now to FIG. 79, one embodiment of the tube 500 or elongate delivery device is shown penetrating through tissue T and delivering the anchor 504. Arrow 510 indicates that rotation of the delivery device 500 will cause the distal end 502 of the device 500 to engage tissue and draw the entire device 500 into and through the tissue. In some embodiments, anchor 504 may have a sharpened tip as indicated by dotted line 512 to allow the anchor 504 to be driven through the tissue.

Figure 80:
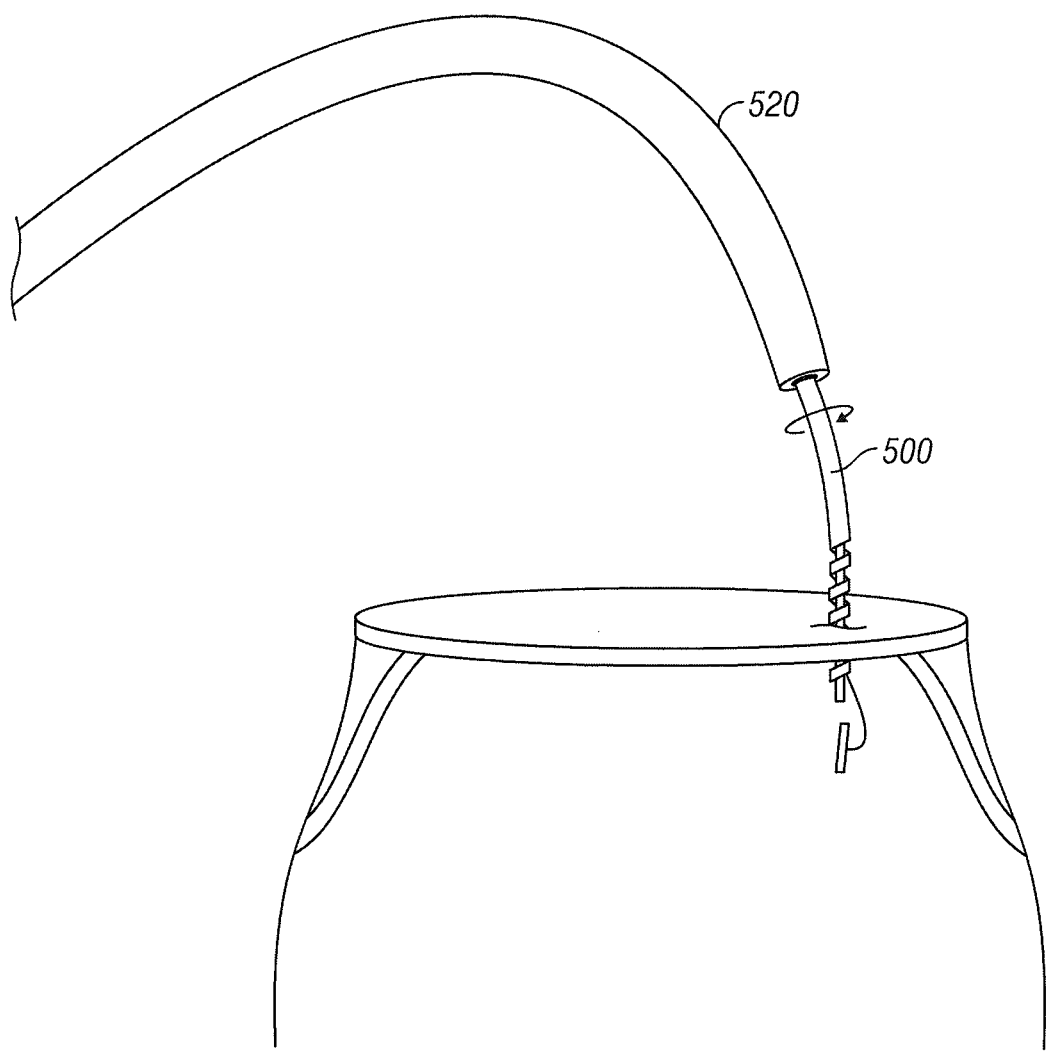

Referring now to FIG. 80, in this embodiment, a guide catheter 520 may be used to guide the elongate delivery device 500 into the correct location for penetration into tissue T. It should be understood that the tube or device 500 may have any of the distal tips disclosed herein and may be used with any combination of anchors disclosed herein. The tube 500 may be rotated within the guide catheter 520 to enable the front end of the tube 500 to engage tissue. In other embodiments, the tube 500 is simply pushed forward to pierce the tissue T.

Figure 81:
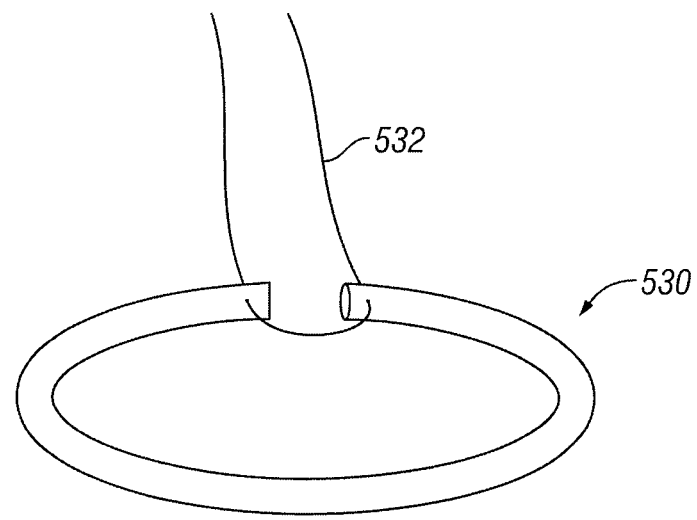
Figure 82:
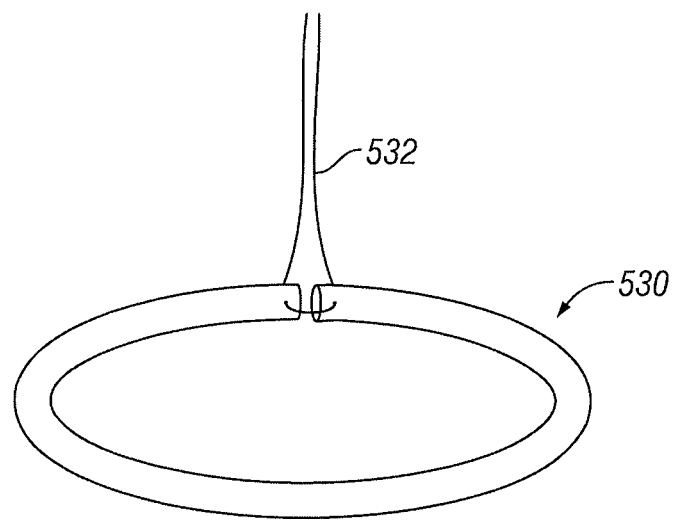

Referring now to FIGS. 81 and 82, the support member 530 after being delivered to a target site, may use a suture 532 to tighten the tissue coupled to the support member 530. The member 530 may be secured by anchors or sutures as described in regards to FIGS. 14A-14C and FIG. 51.

Figure 83:
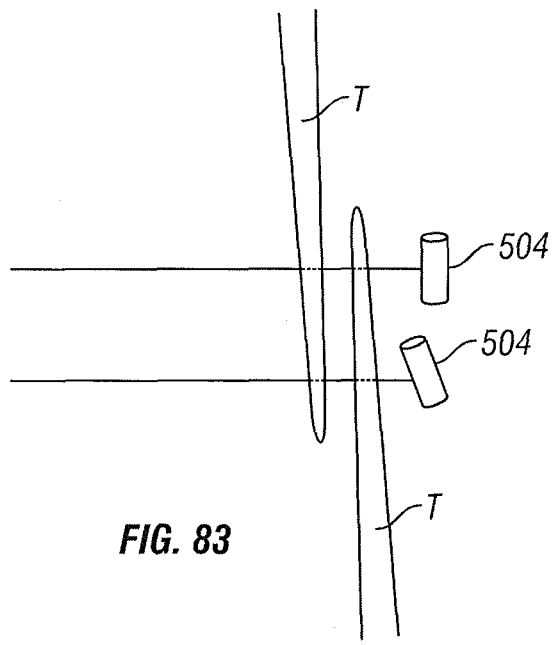
Figure 84:
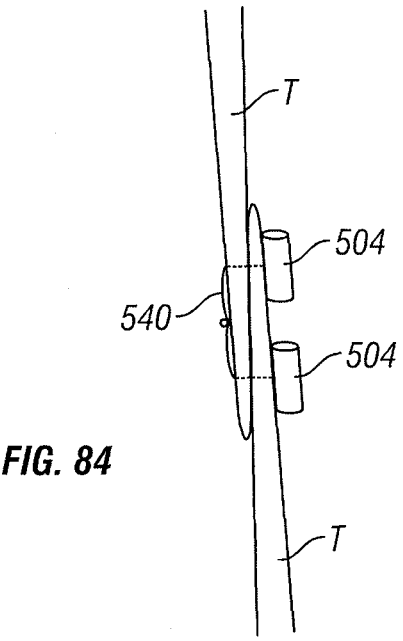

Referring now to FIGS. 83 and 84, the anchors 504 may be delivered through tissue using a delivery device 500 or the like to send an anchor 504 through tissue T. This technique may be useful in patent foramen ovale (PFO) closure in heart tissue. As seen, a suture 540 with anchors 504 may be used for tissue connection.

Figure 85:
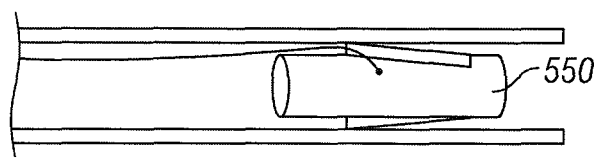
Figure 86:
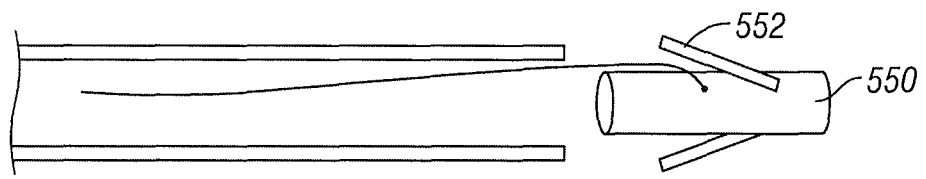

Referring now to FIGS. 85 and 86, a still further embodiment of an anchor 550 is shown. The anchor 550 has outward extending member 552 or barbs which will secure the anchor in tissue after delivery from the catheter 500. This may be useful in situations where the anchor 550 does not fully penetrate through tissue and may rely on the barbs for anchoring force.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, the geometric configuration of the loops of device 10 or 210 may be varied as desired to provide leaflet support, including shapes such as square, triangular, bowed, rounded, or other configuration. The wire loop elements may also be replaced by solid elements, such as a solid, oar shaped clamp instead of a wire loop. Although device 10 is generally shown to have a circular relaxed configuration, it should also be understood that, in all embodiments, the device may have a square, rectangular, triangular, polygonal, or other shape that will provide suitable reduction of valve regurgitation. Additionally, bringing together tissues in closer proximity to one another is one method for closing wounds such as catheter puncture sites during percutaneous procedures (angioplasty, stenting, endograft procedures and the like), as well as in stomach stapling for the morbidly obese, gastrostomy placement, etc. These procedures all may benefit from the inventions described herein. Additionally, any of the inventions and devices described in this application may be manufactured, at least in part, using animal, human or cultured cells and tissues incorporated in whole or in part. These tissues may be harvested or cultured though tissue engineering or altered by the manipulation of their genetic content. In such a manner, these devices may be incorporated into the target location easier, may be less prone to rejection by the body, or may elude certain chemicals and/or enzymes that may be beneficial to the targeted tissues or the body as a whole.

Expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. A tissue anchor assembly, comprising;
 a helical tissue anchor capable of piercing tissue through rotation,
 a suture coupled to a distal end of the helical tissue anchor and configured to provide that as more force is applied to the helical tissue anchor by the suture, the helical tissue anchor collapses upon itself and provides additional support to tissues in which it is attached;
 a tissue support member;
 a clamp coupled to the suture to provide tension between the tissue support member and the anchor, and
 a releasable elongated delivery device with a distal end configured to releasably engage the anchor, the elongated delivery device including engagement threads that allow rotation of the helical tissue anchor for securement.

2. The assembly of claim 1, wherein at least a portion of the tissue support member is a mesh slideably coupled to the suture.

3. The assembly of claim 1, wherein the anchor has a helix geometric configuration.

4. The assembly of claim 1, wherein the anchor is made of at least one of metal or a polymer.

5. The assembly of claim 1, wherein at least a portion of the anchor is sufficiently porous to provide for tissue in-growth.

6. The assembly of claim 1, wherein the anchor includes medicamant delivery to tissue.

7. The assembly of claim 1, wherein the anchor incorporates at least one of, a healing hormone or a composition that provides a therapeutic response to tissue.

8. The assembly of claim 1, wherein the suture is at least one of, a monofilament and a braided multifilament.

9. The assembly of claim 1, wherein the suture is made of a material that is absorbable.

10. The assembly of claim 1, wherein the suture is configured to deliver a medicament to tissue.

11. The assembly of claim 1, wherein the suture is porous to promote tissue in-growth.

12. The assembly of claim 1, wherein at least a portion of the tissue support member is made of mesh.

13. The assembly of claim 12, wherein the mesh is configured to provide support to at least one of a urethra and bladder.

14. The assembly of claim 12, wherein the mesh is configured to provide support to a vagina.

15. The assembly of claim 12, wherein the mesh is woven of a monofilament.

16. The assembly of claim 12, wherein the mesh is made of a polymer.

17. The assembly of claim 12, wherein the mesh is configured to deliver a medicament to tissue.

18. The assembly of claim 12, wherein the medicament is selected from at least one of, estrogen, estrodiol, a substance that promotes tissue in-growth and a substance that provides a therapeutic response to tissue.

* * * * *